(12) United States Patent
Moussy et al.

(10) Patent No.: US 7,727,731 B2
(45) Date of Patent: Jun. 1, 2010

(54) POTENT, SELECTIVE AND NON TOXIC C-KIT INHIBITORS

(75) Inventors: Alain Moussy, Paris (FR); Patrice Dubreuil, Marseilles (FR); Olivier Hermine, Palaiseau (FR)

(73) Assignee: AB Science, Paris (FR)

( * ) Notice: Subject to any disclaimer, the term of this patent is extended or adjusted under 35 U.S.C. 154(b) by 567 days.

(21) Appl. No.: 10/482,037

(22) PCT Filed: Jun. 28, 2002

(86) PCT No.: PCT/IB02/03296

§ 371 (c)(1),
(2), (4) Date: Dec. 29, 2003

(87) PCT Pub. No.: WO03/003006

PCT Pub. Date: Jan. 9, 2003

(65) Prior Publication Data

US 2006/0166281 A1   Jul. 27, 2006

Related U.S. Application Data

(60) Provisional application No. 60/301,404, filed on Jun. 29, 2001.

(51) Int. Cl.
*C12Q 1/02* (2006.01)
*C12Q 1/18* (2006.01)
*C12Q 1/48* (2006.01)
*G01N 33/566* (2006.01)

(52) U.S. Cl. .................... 435/7.21; 435/6; 435/7.24; 435/7.8; 435/15; 435/29; 435/32; 435/377; 436/501

(58) Field of Classification Search .......... 435/6, 435/7.21, 7.24, 7.8, 15, 29, 32, 377; 436/501
See application file for complete search history.

(56) References Cited

U.S. PATENT DOCUMENTS

| | | | |
|---|---|---|---|
| 3,467,666 A | 9/1969 | Dexter et al. | |
| 3,558,653 A | 1/1971 | Coyne et al. | |
| 3,725,403 A | 4/1973 | Krapcho | |
| 4,587,342 A | 5/1986 | Daluge et al. | |
| 5,521,184 A * | 5/1996 | Zimmermann | 514/252.11 |
| 5,639,757 A | 6/1997 | Dow et al. | |
| 5,792,783 A | 8/1998 | Tang et al. | |
| 5,886,020 A | 3/1999 | Tang et al. | |
| 5,916,769 A | 6/1999 | Olsen et al. | |
| 5,952,374 A | 9/1999 | Clarkson | |
| 6,114,371 A | 9/2000 | Tang et al. | |
| 6,133,305 A | 10/2000 | Tang et al. | |
| 6,235,746 B1 | 5/2001 | Davis et al. | |
| 6,420,382 B2 | 7/2002 | Fraley et al. | |
| 6,498,165 B1 | 12/2002 | Armstrong et al. | |
| 6,498,176 B1 | 12/2002 | Lackey et al. | |
| 6,544,988 B1 | 4/2003 | Bilodeau et al. | |
| 6,762,180 B1 * | 7/2004 | Roth et al. | 514/228.2 |
| 6,958,335 B2 | 10/2005 | Buchdunger et al. | |
| 2002/0010203 A1 | 1/2002 | Lipson et al. | |
| 2002/0052386 A1 | 5/2002 | Armistead et al. | |
| 2003/0045451 A1 | 3/2003 | Bacus | |
| 2003/0091974 A1 * | 5/2003 | Moussy et al. | 435/4 |
| 2003/0176443 A1 | 9/2003 | Stein-Gerlach et al. | |
| 2004/0028673 A1 | 2/2004 | Netzer et al. | |
| 2004/0110810 A1 | 6/2004 | Ciufolini et al. | |
| 2004/0241226 A1 | 12/2004 | Moussy et al. | |
| 2004/0242601 A1 | 12/2004 | Moussy et al. | |
| 2004/0242612 A1 | 12/2004 | Moussy et al. | |
| 2004/0259892 A1 | 12/2004 | Moussy et al. | |
| 2004/0259893 A1 | 12/2004 | Moussy et al. | |
| 2004/0266771 A1 | 12/2004 | Moussy et al. | |
| 2004/0266797 A1 | 12/2004 | Moussy et al. | |
| 2004/0266801 A1 | 12/2004 | Moussy et al. | |
| 2005/0054617 A1 | 3/2005 | Moussy et al. | |
| 2005/0059688 A1 | 3/2005 | Moussy et al. | |
| 2005/0089838 A1 | 4/2005 | Moussy et al. | |
| 2005/0176687 A1 | 8/2005 | Moussy et al. | |
| 2005/0222091 A1 | 10/2005 | Moussy et al. | |
| 2006/0166281 A1 | 7/2006 | Moussy et al. | |
| 2006/0204459 A1 | 9/2006 | Moussy et al. | |
| 2006/0275769 A1 * | 12/2006 | Moses et al. | 435/6 |

FOREIGN PATENT DOCUMENTS

DE   198 24 922 A   12/1999

(Continued)

OTHER PUBLICATIONS

Ma, et al., "Indolinone Derivatives Inhibit Constitutively Activated KIT Mutants and Kill Neoplastic Mast Cells", Journal of Investigative Dermatology, Feb. 2000, pp. 392-394, vol. 114, No. 2.

Imokawa, G. "Paracrine cytokine mechanisms of epidermal hyperpigmentation in UVB-melanosis, lentigo senilis and dematofibroma,", Pigment Cell Research, 2002, p. 34, vol. 15 Supp. 9.

James M. Grichnik, et al., "The SCF/KIT Pathway Plays a Critical Role in the Control of Normal Human Melanocyte Homeostasis," The Journal of Investigative Dermatology, vol. 111, No. 2, pp. 233-238, Aug. 1998, XP001133837.

Hattori, H. et al., "The role of the epidermal stem cell factor (SCF)/c-kit cascade in the hyperpigmentation mechanism of lentigo senilis (LS)," Pigment Cell Research, 2002, p. 58, vol. 15, Supp. 9.

(Continued)

Primary Examiner—David A Saunders
(74) Attorney, Agent, or Firm—Sughrue Mion, PLLC

(57) ABSTRACT

The present invention relates to a screening method allowing the identification and selection of compounds targeting the transphosphorylase (also called phosphotransferase) domain of c-kit, more particularly compounds selected to be potent inhibitors of constitutively activated c-kit, while being unable to inhibit other activation pathways as for example the pathways leading to death of IL-3 dependent cells cultured in presence of IL-3.

24 Claims, 1 Drawing Sheet

FOREIGN PATENT DOCUMENTS

Figure 1:
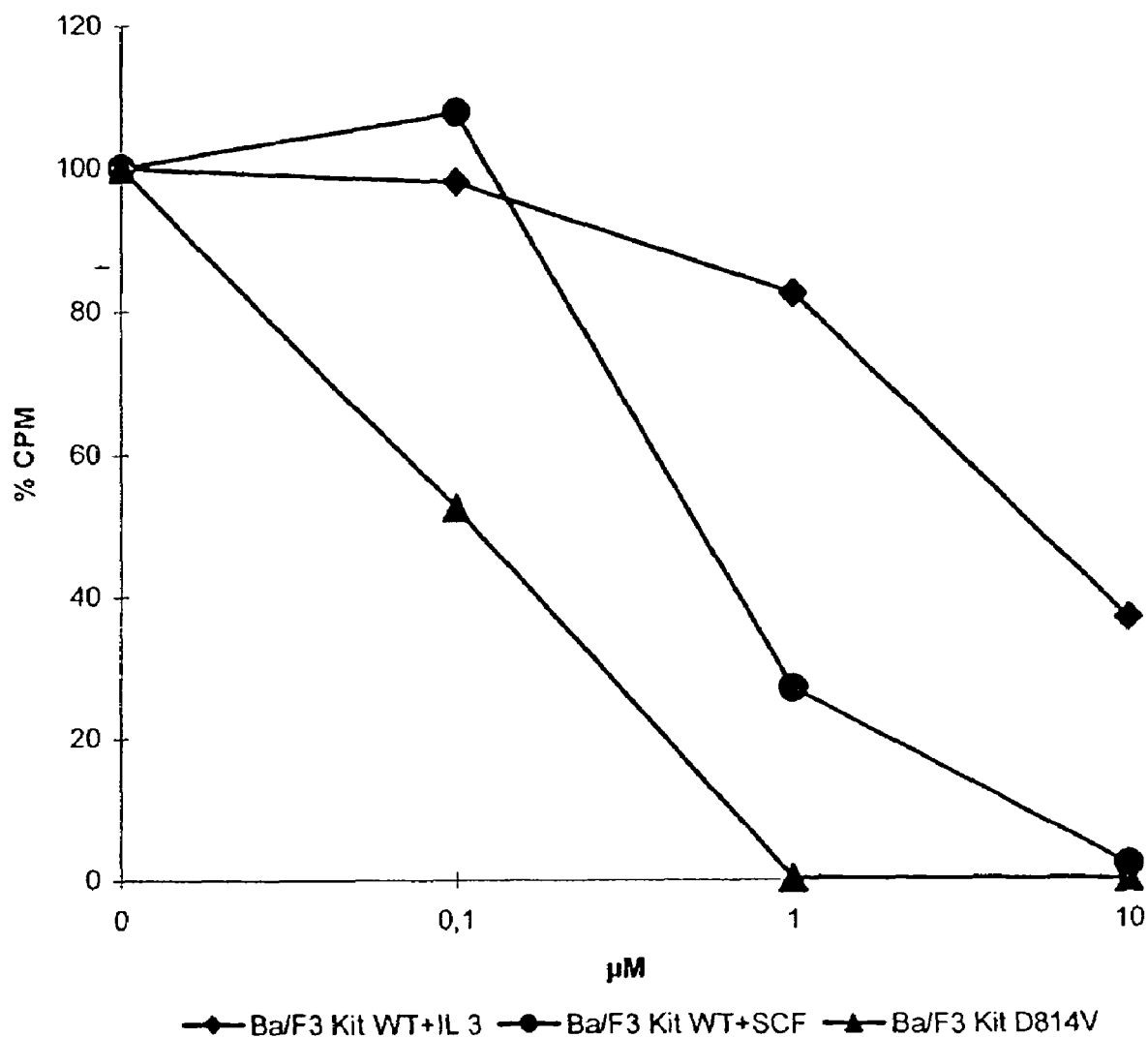

| | | |
|---|---|---|
| DE | 198 44 003 A | 3/2000 |
| EP | 0 403 238 A2 | 12/1990 |
| EP | 0 564 409 A | 10/1993 |
| EP | 0 586 020 A | 3/1994 |
| WO | WO 98 18782 | 5/1998 |
| WO | WO 98 35056 A | 8/1998 |
| WO | WO 98 41525 A | 9/1998 |
| WO | WO 98 50356 A | 11/1998 |
| WO | WO 98/55152 A1 | 12/1998 |
| WO | WO 99/03854 A1 | 1/1999 |
| WO | WO 99 61028 A | 2/1999 |
| WO | WO 99 11643 A | 3/1999 |
| WO | WO 99 15500 A | 4/1999 |
| WO | WO 99 21859 A | 5/1999 |
| WO | WO 99 61422 A | 12/1999 |
| WO | WO 99 65908 A | 12/1999 |
| WO | WO 00 09098 A | 2/2000 |
| WO | WO 00 40971 A | 7/2000 |
| WO | WO 00 55139 A | 9/2000 |
| WO | WO 00 56709 A | 9/2000 |
| WO | WO 00 67794 A | 11/2000 |
| WO | WO 00 73297 A | 12/2000 |
| WO | WO 01 16130 A | 3/2001 |
| WO | WO 01/27081 A1 | 4/2001 |
| WO | WO 01 45689 A | 6/2001 |
| WO | WO 01 47517 A | 7/2001 |
| WO | WO 01 47950 A | 7/2001 |
| WO | WO 01 49287 A | 7/2001 |
| WO | 0164200 A2 | 9/2001 |
| WO | 0164674 A1 | 9/2001 |
| WO | WO 01 90104 A | 11/2001 |
| WO | WO 02 40486 A | 5/2002 |
| WO | WO 02 55517 A | 7/2002 |
| WO | WO 02 072578 A | 9/2002 |
| WO | 02080925 A1 | 10/2002 |
| WO | WO 03 002106 A3 | 1/2003 |
| WO | WO 03 035049 A2 | 5/2003 |
| WO | WO 03 035050 A2 | 5/2003 |
| WO | 03062215 A1 | 7/2003 |

OTHER PUBLICATIONS

A. D. Laird et al, "SU668 Is a Potent Antiangiogenic and Antitumor Agent that Induces Regression of Established Tumors", *Cancer Research*, vol. 60, pp. 4152-4160, 2000.
B. Smolich et al, "The antiangiogenic protein kinase inhibitors SU5416 and SU6668 inhibit the SCF receptor (c-kit) in a human myeloid leukemia cell line and in acute myeloid leukemia blasts", *Blood*, vol. 97, No. 5, pp. 1413-1421, 2001, XP002229742.
Sinha et al., "Implications for Src Kinases in Hematopoiesis: Signal Transduction Therapeutics", *Journal of Hematotherapy & Stem Cell Research*, vol. 8, pp. 465-480, 1999.
Sinha and Corey, *Signal Transduction Therapeutics*, pp. 471-480, 1999.
Asthma and Bone Health, *NIHORBD-NRC Fact Sheets*, 4 pages, Dec. 2005.
J. Lesinski, "Preventing Bone Loss", The Connection Newspapers, pp. 1-2, May 28, 2003.
www.hopkinsmedicine.org, Bone Loss from Chemotherapy, *Journal of Clinical Oncology*, vol. 19(14); pp. 3306-3311, 2001.
Dolan et al., Rheumatology 41, www.rheumatology.oxfordjournals.org, pp. 1047-1051, 2002.
NIH Osteoporosis and Related Bone Diseases-National Resource Center, "What People With Inflammatory Bowel Disease Need to Know About Osteoporosis", pp. 1-4, updated Feb. 2005.
Krystal G W, et al., "Indolonone Tyrosine Kinase Inhibitors Block Kit Activation and Growth of Small Cell Lung Cancer Cells", vol. 61, No. 9, May 1, 2001, pp. 3660-3668.
Moosa, Mohammadi et al, "Structures of the Tyrosine Kinase Domain of Fibroblast Growth Factor Receptor in Complex with Inhibitors", *Science*, vol. 276, No. 5314, pp. 955-960, 1997.
Defazio, et al., "Interferon β-1a downregulates TNF α-induced intercellular adhesion molecule 1 expression on brain microvascular endothelial cells through a tyrosine kinase-dependent pathway", *Brain research*, vol. 881 (2): pp. 227-230, 2000.
J. Topaly, et al., Synergistic activity of the new ABL-specific tyrosine kinase inhibitor STI571 and chemotherapeutic drugs on BCR-ABL-positive chronic myelogenous leukemia cells, *Leukemia*, vol. 15, pp. 342-347, 2001.
www.gsdl.com, "Laboratory Assessments: IBD and Allergies," GSDL Inflammatory Bowel Disease (IBD) and Allergies, 2 pages, Dec. 2005.
www.health.ucsd.edu, "Researchers Show Beneficial Role of Bacterial DNA in Fighting Inflammatory Bowel Disease," UCSD School of Medicine News Health Sciences Communications, 2 pages, Apr. 2002.
J. Jahnsen, et al., "Bone mineral density in patients with inflammatory bowel disease: a population-based prospective two-year follow-up study", Scand. J. Gastroenterol. Feb. 2004; 39(2), abstract only.
H. Mielants, et al., "Course of gut inflammation in spondylarthropathies and therapeutic consequences," Bailliers Clin. Rheumatol. Feb. 1996; 10(1): abstract only.
A. Yamataka, et al., Localization of Intestinal Pacemaker Cells and Synapses in the Muscle Layers of a Patient with Colonic Hypoganglionosis, *Journal of Pediatric Surgery*, vol. 31, No. 4, pp. 584-587, 1996.
A. Yamataka, et al., A Lack of Intestinal Pacemaker (c-kit) in Aganalionic Bowel of Patients with Hirschsprung's Disease, *Journal of Pediatric Surgery*, vol. 30, No. 3, pp. 441-444, 1995.
R. Hicks, "Rheumatoid Arthritis", www.bbc.co.uk, 2 pages, Dec. 2005.
Tada S, et al., "The significance of soluble IL-2 receptors in rheumatoid arthritis with interstitial pneumonia", *Aerugi*, vol. 41(3), pp. 428-433, 1992.
S. P. Singh et al.: "Synthesis of some new 5 Bromo-3-Arylthiosemicarbazone-2-Indolinones as Antimicrobial Agents" *ACTA Pharmaceutica Jugoslavica*, vol. 36, No. 1, pp. 19-26, XP008014269; ISSN: 0001-6667 (1986).
Adel A. El-Gendy et al.: Synthesis and Antimicrobial Actibity of Some New 2-indolinone derived ozimes and spiro-isoxazolines.: *Archives of Pharmacol Research* (SEOUL), vol. 23, No. 4, Aug. 2000, pp. 310-314, XP008014265; ISSN: 0253-6269.
A K S Gupta, et al.: "Synthesis of Some New Indolinone Derived hydrazones as Possible, Anti Bacterial Agents", *European Journal of Medicinal Chemistry*, vol. 18, No. 2, 1983, pp. 181-184, XP001109724; ISSN: 0223-5234.
S P Singh, et al.: "Indolinone Derivatives as Potential Antimicrobilal Agents" *Zentralblatt Fuer Mikrobiologie*, vol. 144, No. 2, 1989, pp. 105-109, XP008014264; ISSN: 0232-4393 (1989).
Marcus Maurer et al.: "The C-kit Ligand, Stem Cell Factor, can enhance innate immunity through effects on mast cells." *Journal of Experimental Medicine*, vol. 188, No. 12, Dec. 21, 1998, pp. 2343-2348, XP008014256; ISSN: 0022-1007.
Gary R. Klimpel et al.: "A Role for Stem Cell Factor (SCF): C-kit Interaction(s) in the Intestinal Tract Response to *Salmonell typhimurium* Infection.." *Journal of Experimental Medicine*, vol. 184, No. 1, 1996, pp. 271-276, XP008014258, ISSN: 0022-1007.
Stephen J. Galli et al.: "Mast Cells as Sentinels of Innate Immunity." *Current Opinion in Immunology*, vol. 11, No. 1, Feb. 1999, pp. 53-59, XP004257657, ISSN: 0952-7915.
Medicine House, "Inflammatory Pain Syndromes Arthritis", www.medicinehouse.com, 13 pages, Jan. 2006.
D. Hollander, "Interstital Cystitis and Silk Allergy", *Med. Hypotheses*, vol. 43, pp. 155-156, 1994.
T. Maher et al., "Arthritis Rhinitis: Nothing to Sneeze At", Massachusetts College of Pharmacy and Health Sciences Continuing Education pp. 1-23, Jun. 2002.
D. Hele, "New approaches to modulation of inflammatory processes in airway disease models", *Respiratory research*, vol. 2, No. 5, 4 pages, 2001.
C. Oetzel, et al., The Tyrosine Kinase Inhibitor CGP 57148 (STI 571) Induces Apoptosis in BCR-ABL-positive Cells By Down-Regulating BCL-X, *Clin. Cancer Research*, vol. 6, pp. 1958-1968, 2000.
M. Carroll et al., "CGP 57148, a Tyrosine Kinase Inhibitor, Inhibits the Growth of Cells Expressing BCR-ABL, TEL-ABL, and TEL-PDGFR Fusion Proteins" *Blood*, vol. 90, No. 12, pp. 4947-4952, 1997.

P. Ferrao, Expression of Constitutively Activated Human c-Kit in Myb Transformed Early Myeloid Cells Leads to Factor Independence, Histiocytic Differentiation, and Tumorigencity, *Blood*, vol. 90, No. 11, pp. 4539-4552, 1997.

M. Heinrich, "Inhibition of c-kit receptor tyrosine kinase activity by STI-571, a selective tyrosine kinase inhibitor", *Blood*, vol. 96, No. 3, pp. 925-932, 2000, XP001097629.

G. Bold, "New Anilinophthalazines as Potent and Orally Well Absorbed Inhibitors of the VEGF Receptor Tyrosine Kinases Useful as Antagonists of Tumor-Driven Angiogenesis", *J Med. Chem*, vol. 43, pp. 2310-2323, 2000, XP000971347.

P. Traxler, "Protein tyrosine kinase inhibitors in cancer treatment", *Exp. Opin. Ther. Patents*, vol. 7, No. 6, pp. 571-585, XP002122590, 1997.

Srinivasan, Radhika, Interstital Cystitis Association, "Inflammatory Bowel Disease", www.ichelp.com, 2 pages, Jan. 2006.

R. Saban, "Mast cell regulation of inflammation and gene expression during antigen-induced bladder inflammation in mice", *Physiol Genomics*, vol. 7, pp. 35-43, 2001, XP001161208.

H. Nechustan, et al., Regulation of mast cell growth and proliferation, *Clin. Reviews in Oncology*, vol. 23, pp. 131-150, 1996, XP008019233.

S. Wilkinson et al, "Selective tyrosine kinase inhibitors", *Emerging Drugs*, vol. 5, No. 3, pp. 287-297, XP001062304 (2000).

J. Wood et al., "PTK787/ZK 222584, a Novel and Potent Inhibitor of Vascular Endothelial Growth Factor Receptor Tyrosine Kinases, Impairs Vascular Endothelial Growth Factor induced Responses and Tumor Growth after Oral Administration", *Cancer Research*, vol. 60, pp. 2178-2189, 2000, XP000971163.

Non-Final Office Action issued, dated Jan. 12, 2006 in U.S. Appl. No. 10/482,039.

Response to Non-Final Office Action filed Apr. 12, 2006 in U.S. Appl. No. 10/482,039.

Non-Final Office Action issued, dated Jul. 18, 2006 in U.S. Appl. No. 10/482,039.

Response to Non-Final Office Action filed Jan. 18, 2007 in U.S. Appl. No. 10/482,039.

Non-Final Office Action issued, dated Apr. 11, 2007 in U.S. Appl. No. 10/482,039.

Response to Non-Final Office Action filed Jul. 11, 2007 in U.S. Appl. No. 10/482,039.

Restriction Requirement issued, dated Mar. 29, 2007 in U.S. Appl. No. 10/482,177.

Response to Restriction Requirement filed May 25, 2007 in U.S. Appl. No. 10/482,177.

Non-final Office Action issued, dated Aug. 17, 2007 in U.S. Appl. No. 10/482,177.

Non-final Office Action issued, dated Jan. 18, 2006 in U.S. Appl. No. 10/490,348.

Response to Non-final Office Action filed Apr. 18, 2006 in U.S. Appl. No. 10/490,348.

Non-final Office Action issued, dated Jul. 17, 2006 in U.S. Appl. No. 10/490,348.

Response to Non-final Office Action issued, dated Jan. 17, 2007 in U.S. Appl. No. 10/490,348.

Non-final Office Action issued, dated Aug. 22, 2007 in U.S. Appl. No. 10/490,348.

Restriction Requirement issued, dated Apr. 19, 2007 in U.S. Appl. No. 10/505,842.

Response to Restriction Requirement filed Aug. 17, 2007 in U.S. Appl. No. 10/505,842.

Non-final Office Action issued, dated Sep. 10, 2007 in U.S. Appl. No. 10/505,842.

Non-final Office Action issued, dated Jan. 6, 2006 in U.S. Appl. No. 10/482,033.

Response to Non-final Office Action filed May 5, 2006 in U.S. Appl. No. 10/482,033.

Non-final Office Action issued, dated Jul. 28, 2006 in U.S. Appl. No. 10/482,033.

Response to Non-final Office Action filed Nov. 28, 2006 in U.S. Appl. No. 10/482,033.

Non-final Office Action issued, dated Apr. 9, 2007 in U.S. Appl. No. 10/482,033.

Response to Non-final Office action filed Sep. 10, 2007 in U.S. Appl. No. 10/482,033.

International Search Report dated Jan. 31, 2003 for International Application No. PCT/IB02/03296.

International Search Report dated Feb. 24, 2003 for International Application No. PCT/IB02/03295.

International Search Report dated Mar. 31, 2003 for International Application No. PCT/IB02/03317.

International Search Report dated Jul. 9, 2003 for International Application No. PCT/IB02/04251.

International Search Report dated Nov. 6, 2003 for International Application No. PCT/IB02/04236.

International Search Report dated Sep. 2, 2003 for International Application No. PCT/IB03/01425.

Non-final Office Action issued, dated Jan. 20, 2006 in U.S. Appl. No. 10/482,035.

Response to Non-final Office Action filed Apr. 20, 2006 in U.S. Appl. No. 10/482,035.

Non-final Office Action issued, dated Nov. 2, 2006 in U.S. Appl. No. 10/482,035.

Response to Non-final Office Action filed Feb. 2, 2007 in U.S. Appl. No. 10/482,035.

Final Office Action issued, dated May 16, 2007 in U.S. Appl. No. 10/482,035.

Non-final Office Action issued, dated Jun. 4, 2007 in U.S. Appl. No. 10/490,334.

Longley, B.J., et al., "New Approaches to Therapy for Mastocytosis a Case for Treatment with Kit Kinase Inhibitors", Hematology-Oncology Clinics of North America, W.B. Saunders, U.S., vol. 14, No. 3, Jun. 2000, pp. 689-695.

Marya F. McCarty, et al., "Overexpression of PDGF-BB decreases colorectal and pancreatic cancer growth by increasing tumor pericyte content", The Journal of Clinical Investigation, 2007, 117(8): 2114-2122.

A. Hachiya et al., The Inhibitory Effect of an Extract of Clove (*Syzygium aromaticum*, (L.) Merr. Et Perry) on Ultraviolet B-Induced Pigmentation Via Inhibition of Stem Cell Factor/c-kit Signaling, Journal of Investigative Dermatology, Jul. 2002, vol. 119(1): 341.

Christopher F. Njeh et al, "Bone Loss: Quantitative imaging techniques for assessing bone mass in rheumatoid arthritis", Arthritis Research, 2000, 2(6): 446-450.

"Inflammatory Bowel Disease: Frequently Asked Questions", www.healingwell.com/library/ibd/faq3.asp, Last Modified Mar. 15, 1997.

Andrea König et al.: "Downregulation of C-*kit* Expression in Human Endothelial Cells by Inflammatory Stimuli", Blood, 1997, 90(1): 148-155.

Final Office Action dated Nov. 29, 2007 in U.S. Appl. No. 10/482,033.

Final Office Action dated May 16, 2007 in U.S. Appl. No. 10/482,035.

Request for Continued Examination and 1.114 Amendment filed Nov. 16, 2007 in U.S. Appl. No. 10/482,035.

K.F. Chung, et al. British Medical Bulletin, 1992, 48:179-189 (Abstract only).

www.pueblo.gsa.gov/cic_text/health/atopic-dermatitis/defining.html, Jan. 22, 2000.

Final Office Action dated Oct. 3, 2007 in U.S. Appl. No. 10/482,039.

Request for Continued Examination and Response to Final Office Action filed Mar. 3, 2008 in U.S. Appl. No. 10/482,039.

1.111 Amendment filed Feb. 19, 2008 in U.S. Appl. No. 10/482,177.

Final Office Action dated May 29, 2008 in U.S. Appl. No. 10/482,177.

Wei Zhang et al., "Modulation of Tumor Angiogenesis by Stem Cell Factor", Cancer Research, 2000, 60: 6757-6762.

Restriction and Election of Species Requirements dated Oct. 15, 2007 in U.S. Appl. No. 10/482,758.

Response to Restriction and Election of Species Requirements filed Mar. 14, 2008 in U.S. Appl. No. 10/482,758.

Restriction Requirement issued, dated Oct. 2, 2007 in U.S. Appl. No. 10/490,287.

Response to Restriction Requirement filed Jan. 2, 2008 in U.S. Appl. No. 10/490,287.

Non-Final Office Action dated Mar. 18, 2008 in U.S. Appl. No. 10/490,287.

Frederic Feger et al., "The role of mast cells in host defense and their subversion by bacterial pathogens," Trends in Immunology, 2002, 23(3): 151-158.

Mosby's GenRx: The Complete Reference for Generic and Brand Drugs, 1998, pp. II-1991 to II-1994.

1.111 Amendment filed Dec. 4, 2007 in U.S. Appl. No. 10/490,334.

Non-Final Office Action dated Feb. 20, 2008 in U.S. Appl. No. 10/490,334.
1.111 Amendment filed May 20, 2008 in U.S. Appl. No. 10/490,334.
1.111 Amendment filed Dec. 21, 2007 in U.S. Appl. No. 10/490,348.
1.111 Amendment filed Dec. 10, 2007 in U.S. Appl. No. 10/505,842.
Final Office Action dated Mar. 13, 2008 in U.S. Appl. No. 10/505,842.
Request for Continued Examination and 1.114 Response filed Mar. 28, 2008 in U.S. Appl. No. 10/482,033.
Non-Final Office Action dated Jun. 5, 2008 in U.S. Appl. No. 10/482,039.
Non-Final Office Action dated Jan. 30, 2008 in U.S. Appl. No. 10/482,035.
Non Final Office Action dated Jun. 17, 2008 in U.S. Appl. No. 10/482,758.
Patrick D. W. Kiely et al., "Mercuric Chloride-Induced Vasculitis in the Brown Norway Rat: αβ T Cell-Dependent and -Independent Phases", The Journal of Immunology, 1997, 159:5100-5106.
Non-Final Office Action dated Jun. 11, 2008 in U.S. Appl. No. 10/482,033.
Mary B. Edelson et al., "Circulating Pro- and Counterinflammatory Cytokine Levels and Severity in Necrotizing Enterocolitis", Pediatrics, 1999, 103(4): 766-771. (Abstract Only).
Restriction and Election of Species Requirements dated Jun. 9, 2008 in U.S. Appl. No. 10/490,286.
Non-Final Office Action dated Jun. 25, 2008 in U.S. Appl. No. 10/490,348.
F. Aldenborg et al., "Proliferation and transepithelial migration of mucosal mast cells in interstitial cystitis", Immunology, 1986, 58:411-416.
M. Hohenfellner et al., "Interstitial cystitis: increased sympathetic innervation and related neuropeptide synthesis", J. Urol. 1992, 147(3):Abstract Only.
1.111 Response filed Jul. 30, 2008 in U.S. Appl. No. 10/482,035.
1.111 Amendment filed Aug. 18, 2008 in U.S. Appl. No. 10/490,287.
Non-Final Office Action dated Aug. 21, 2008 in U.S. Appl. No. 10/490,334.
Final Office Action dated Oct. 24, 2008 in U.S. Appl. No. 10/482,035.
David A. Walsh et al., "Angiogenesis in the pathogenesis of inflammatory joint and lung diseases", Arthritis Research, 2001, 3(3): 147-153.
Request for Continued Examination and 1.114 Amendment filed Dec. 1, 2008 in U.S. Appl. No. 10/482,177.
1.111 Amendment filed Sep. 25, 2008 in U.S. Appl. No. 10/490,348.
Notice of Appeal filed Dec. 5, 2008, in U.S. Appl. No. 10/482,039.
Notice of Appeal filed Dec. 11, 2008, in U.S. Appl. No. 10/482,033.
1.111 Amendment filed Dec. 17, 2008, in U.S. Appl. No. 10/482,758.
Fahad A. Al-Obeidi et al., "Development of inhibitors for protein tyrosine kinases", Oncogene, 2000, 19: 5690-5701.
F. Dazzi et al., "Normal and Chronic phase CML hematopoietic cells repopulate NOD/SCID bone marrow with different kinetics and cell lineage representation", Hematol. J., 2000, 1(5):307-315.
Ariel Fernandez et al., "An anticancer C-Kit kinase inhibitor is reengineered to make it more active and less cardiotoxic", The Journal of Clinical Investigation, 2007, 117(12): 4044-4054.
B. Foxwell et al., "Prospects for the development of small molecular weight compounds to replace anti-tumour necrosis factor biological agents", Ann Rheum Dis, 2003, 62 (Suppl. II): ii90-ii93.
C. Gelbmann et al., "Strictures in Crohn's disease are characterised by an accumulation of mast cells colocalised with laminin but not with fibronectin or vitronectin", Gut, 1999, 45(2):210-217.
Gleevec, http://www.gleevec.com/info/cml/howgleevecworks/sideandsafety.isp.
M.A. Golstein et al., "Chronic Interstitial Cystitis Occurring during the Shift between Rheumatoid Arthritis and Lupus", Clinical Rheumatology, 1994, 13(1): 119-122.
J. Gutknecht et al., "Leukemia and Crohn's Disease", Digestive Diseases and Sciences, 1986, 31(12):1391.

Akira Inoue et al., "Suppression of surfactant protein A by an epidermal growth factor receptor tyrosine kinase inhibitor exacerbates lung inflammation", Cancer Sci., 2008, 99(8): 1679-1684.
International Search Report dated Feb. 16, 2004 for International Application No. PCT/IB03/01071.
Dean D. Metcalfe et al., "Mast Cells", Physiological Reviews, 1997, 77(4): 1033-1079.
S.H. Mir Madjlessi et al., "Inflammatory bowel disease and leukemia. A report of seven cases of leukemia in ulcerative colitis and Crohn's disease and review of the literature", Dig. Dis. Sci., 1986, 10:1025-1031, Abstract.
Lee S. Rosen et al., "Phase I Experience with SU6668, a novel Multiple Receptor Tyrosine Kinase Inhibitor in Patients with Advanced Malignancies", Proc Am Soc Clin Oncol, 2001, 20 (Abstract 383).
Peter Traxler, "Tyrosine kinases as targets in cancer therapy- successes and failures", Expert Opin. Ther. Targets, 2003, 7(2): 215-234.
Peter Vajkoczy et al., "Inhibition of Tumor Growth, Angiogenesis, and Microcirculation by the Novel flk-1 Inhibitor SU5416 as Assessed by Intravital Multi-fluorescence Videomicroscopy", Neoplasia, 1999, 1(1): 31-41.
Request for Continued Examination and 1.114 Response filed Feb. 11, 2009 in U.S. Appl. No. 10/482,033 (Q79217).
Non-Final Office Action mailed Apr. 23, 2009, in U.S. Appl. No. 10/482,033 (Q79217).
Request for Continued Examination and 1.114 Response filed Feb. 23, 2009, in U.S. Appl. No. 10/482,035 (Q79219).
Non-Final Office Action mailed Apr. 29, 2009 in U.S. Appl. No. 10/482,035 (Q79219).
Request for Continued Examination and 1.114 Response filed Feb. 5, 2009, in U.S. Appl. No. 10/482,039 (Q79214).
Non-Final Office Action mailed Apr. 10, 2009 in U.S. Appl. No. 10/482,039 (Q79214).
Notice of Allowance mailed Aug. 26, 2009 in U.S. Appl. No. 10/482,039 (Q79214).
Non-Final Office Action dated Mar. 3, 2009, in U.S. Appl. No. 10/482,177 (Q79223).
Final Office Action mailed Mar. 4, 2009, in U.S. Appl. No. 10/482,758 (Q79213).
Final Office Action dated Jan. 22, 2009, in U.S. Appl. No. 10/490,287 (Q80533).
1.111 Amendment filed Dec. 22, 2008, in U.S. Appl. No. 10/490,334 (Q80535).
Non-Final Office Action mailed Apr. 28, 2009 in U.S. Appl. No. 10/490,334 (Q80535).
Final Office Action dated Jan. 12, 2009, in U.S. Appl. No. 10/490,348 (Q80534).
1.116 Amendment filed Jan. 30, 2009 in U.S. Appl. No. 10/490,348 (Q80534).
Non-Final Office Action mailed Mar. 19, 2009, in U.S. Appl. No. 10/490,348 (Q80534).
Restriction Requirement mailed Jan. 29, 2009, in U.S. Appl. No. 10/505,899 (Q83240).
Restriction Requirement mailed Jan. 19, 2007 in U.S. Appl. No. 10/523,018.
Restriction Requirement mailed Jan. 30, 2007 in U.S. Appl. No. 10/482,034 (Q79224).
Non-Final Office Action mailed Jan. 3, 2006 in U.S. Appl. No. 10/482,036 (Q79221).
1.111 Amendment filed Mar. 23, 2006 in U.S. Appl. No. 10/482,036 (Q79221).
Non-Final Office Action mailed Jul. 20, 2006 in U.S. Appl. No. 10/482,036 (Q79221).
Restriction Requirement mailed Oct. 21, 2005 in U.S. Appl. No. 10/482,040 (Q79222).
Restriction Requirement mailed Jan. 23, 2007 in U.S. Appl. No. 10/482,179 (Q79216).

* cited by examiner

SEQUENCE LISTING

```
<160> NUMBER OF SEQ ID NOS: 5

<210> SEQ ID NO 1
<211> LENGTH: 976
<212> TYPE: PRT
<213> ORGANISM: Homo sapiens
<220> FEATURE:
<223> OTHER INFORMATION: Human c-kit

<400> SEQUENCE: 1

Met Arg Gly Ala Arg Gly Ala Trp Asp Phe Leu Cys Val Leu Leu Leu
 1               5                  10                  15

Leu Leu Arg Val Gln Thr Gly Ser Ser Gln Pro Ser Val Ser Pro Gly
             20                  25                  30

Glu Pro Ser Pro Ser Ile His Pro Gly Lys Ser Asp Leu Ile Val
         35                  40                  45

Arg Val Gly Asp Glu Ile Arg Leu Leu Cys Thr Asp Pro Gly Phe Val
     50                  55                  60

Lys Trp Thr Phe Glu Ile Leu Asp Glu Thr Asn Glu Asn Lys Gln Asn
```

-continued

```
            65                  70                  75                  80
Glu Trp Ile Thr Glu Lys Ala Glu Ala Thr Asn Thr Gly Lys Tyr Thr
                        85                  90                  95
Cys Thr Asn Lys His Gly Leu Ser Asn Ser Ile Tyr Val Phe Val Arg
                100                 105                 110
Asp Pro Ala Lys Leu Phe Leu Val Asp Arg Ser Leu Tyr Gly Lys Glu
                115                 120                 125
Asp Asn Asp Thr Leu Val Arg Cys Pro Leu Thr Asp Pro Glu Val Thr
        130                 135                 140
Asn Tyr Ser Leu Lys Gly Cys Gln Gly Lys Pro Leu Pro Lys Asp Leu
145                 150                 155                 160
Arg Phe Ile Pro Asp Pro Lys Ala Gly Ile Met Ile Lys Ser Val Lys
                165                 170                 175
Arg Ala Tyr His Arg Leu Cys Leu His Cys Ser Val Asp Gln Glu Gly
                180                 185                 190
Lys Ser Val Leu Ser Glu Lys Phe Ile Leu Lys Val Arg Pro Ala Phe
                195                 200                 205
Lys Ala Val Pro Val Val Ser Val Ser Lys Ala Ser Tyr Leu Leu Arg
210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                245                 250                 255
Glu Lys Tyr Asn Ser Trp His His Gly Asp Phe Asn Tyr Glu Arg Gln
                260                 265                 270
Ala Thr Leu Thr Ile Ser Ser Ala Arg Val Asn Asp Ser Gly Val Phe
                275                 280                 285
Met Cys Tyr Ala Asn Asn Thr Phe Gly Ser Ala Asn Val Thr Thr Thr
        290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
                340                 345                 350
Arg Thr Phe Thr Asp Lys Trp Glu Asp Tyr Pro Lys Ser Glu Asn Glu
                355                 360                 365
Ser Asn Ile Arg Tyr Val Ser Glu Leu His Leu Thr Arg Leu Lys Gly
                370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
                420                 425                 430
Phe Pro Glu Pro Thr Ile Asp Trp Tyr Phe Cys Pro Gly Thr Glu Gln
                435                 440                 445
Arg Cys Ser Ala Ser Val Leu Pro Val Asp Val Gln Thr Leu Asn Ser
        450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
```

```
Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
    530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605

Tyr Gly Leu Ile Lys Ser Asp Ala Ala Met Thr Val Ala Val Lys Met
    610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
        675                 680                 685

Phe Ile Cys Ser Lys Gln Glu Asp His Ala Glu Ala Ala Leu Tyr Lys
    690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
        755                 760                 765

Leu Leu Ser Phe Ser Tyr Gln Val Ala Lys Gly Met Ala Phe Leu Ala
    770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
        835                 840                 845

Glu Ser Asp Val Trp Ser Tyr Gly Ile Phe Leu Trp Glu Leu Phe Ser
    850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910
```

```
Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
        930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 2
<211> LENGTH: 30
<212> TYPE: DNA
<213> ORGANISM: Homo sapiens
<220> FEATURE:
<223> OTHER INFORMATION: Primer

<400> SEQUENCE: 2
aagaagagat ggtacctcga ggggtgaccc                              30

<210> SEQ ID NO 3
<211> LENGTH: 33
<212> TYPE: DNA
<213> ORGANISM: Homo sapiens
<220> FEATURE:
<223> OTHER INFORMATION: Primer

<400> SEQUENCE: 3
ctgcttcgcg gccgcgttaa ctcttctcaa cca                          33

<210> SEQ ID NO 4
<211> LENGTH: 20
<212> TYPE: DNA
<213> ORGANISM: Homo sapiens
<220> FEATURE:
<223> OTHER INFORMATION: Primer

<400> SEQUENCE: 4
agctcgttta gtgaaccgtc                                         20

<210> SEQ ID NO 5
<211> LENGTH: 20
<212> TYPE: DNA
<213> ORGANISM: Homo sapiens
<220> FEATURE:
<223> OTHER INFORMATION: Primer

<400> SEQUENCE: 5
gtcagacaaa atgatgcaac                                         20
```

POTENT, SELECTIVE AND NON TOXIC C-KIT INHIBITORS

This application is a National Stage application under 35 U.S.C. §371 of PCT/IB 02/03296, filed Jun. 28, 2002 and claims benefit to U.S. Provisional Application No. 60/301,404, filed Jun. 29, 2001.

The present invention relates to a screening method allowing the identification and selection of compounds targeting the transphosphorylase (also called phosphotransferase) domain of c-kit, more particularly compounds selected to be potent inhibitors of constitutively activated c-kit, while being unable to inhibit other activation pathways such as for example the pathways leading-to-death of IL-3 dependent cells lo cultured in presence of IL-3.

The protooncogene c-kit that encodes the receptor for stem cell factor (SCF) belongs to the type III receptor tyrosine kinase subfamily, characterized by the presence of five Ig-like domains in the extracellular domain and by an interkinase sequence that splits the intracytoplasmic domain into the adenosine triphosphate (ATP)-binding domain and the phosphotransferase domain [1]. Its gene is located on chromosome 4q12 in humans and is encoded by the W locus on murine chromosome 5 [2]. The product of the c-kit gene is a transmembrane receptor composed by 976 amino acids (aa), with 519 extracellular aa, a transmembrane domain of 23 aa and an intracellular tail of 433 aa [3]. The c-kit receptor is normally expressed on various cell types including melanocytes, mast cells, primitive hematopoietic cells, primordial germ cells and interstitial cells of Cajal (ICC) [4]. The ligand for c-kit receptor is a cytokine named stem cell factor (SCF) or Kit ligand (KL), or Steel factor (SL) or mast cell growth factor (MCGF) [5, 6]. This cytokine is encoded by a gene located on chromosome 12 in human and by the Si locus 25 on murine chromosome 10 [7]. The product of this gene is alternatively spliced, leading to a soluble form and/or to a membrane-anchored form [8]. SCF acts either alone or in combination with other growth factors in promoting the survival and self-renewal of stem cells, and the proliferation, differentiation and migration of various cell types: melanocytes. mast cells, primitive hematopoietic cells, germ cells, and ICC. SCF binding to its receptor promotes dimerization of c-kit and induces intrinsic tyrosine kinase activity, resulting in transphosphorylation of particular tyrosine residues [9, 10]. When phosphorylated, these tyrosine residues become docking sites for several intracellular signaling molecules, leading to various cellular responses in different cell types.

However, like it is the case for a number of other kinases, c-kit can be activated without binding its ligand SCF. A number of naturally occurring mutations lead to constitutive activation of the c-kit kinase that results in abnormal cell proliferation and the development of diseases such as mastocytosis and various other cancers. The first activating mutation of c-kit was described in a feline model, induced by the Hardy-Zuckerman 4-feline sarcoma virus encoding the transforming oncogene v-kit, a mutated and truncated viral homologue of c-kit [11]. Recently, receptor mutations leading to constitutive activation of c-kit have been described in mast cell leukemic cell lines and in cells derived from patients with mastocytosis, associated or not with others hematological malignancies. The various activating mutations of c-kit that have been identified so far are described below in details.

A second mechanism leading to an increased activation of c-kit is autocrine secretion of SCF in various tumoral tissues, as in small cell lung cancer (SCLC) [12], colorectal carcinoma [13], breast carcinoma [14], gynecological tumors [15], and neuroblastomas [16].

Tyrosine kinase inhibitors, which have been proposed in the art to inhibit c-kit have not been developed or shown to inhibit activated-mutant c-kit. There are two exceptions detailed below, one of which (STI 571) is not active with our assay, and we will provide here an explanation for the mistaken interpretation of the authors, and the other SU6577 is only active at high concentration at which toxicity is seen.

Heinrich et al. (2000, Blood, Aug. 1, 1996(3):925-32) state that STI 571 (WO 99/03854) has a more potent inhibitory effect on the kinase activity of a mutant in a human mast cell leukemia cell line (HMC-1, expressing a juxtamembrane mutation), than it does on ligand-dependent activation of the wild-type receptor. As a result, this compound could appear useful for treating proliferative diseases involving the activated mutant c-kit but not diseases caused by ligand activated c-kit.

The present invention goes to the opposite direction since the method described in details below is directed to the identification of compounds that are capable of inhibiting activated c-kit whether they are SCF activated c-kit or mutant activated c-kit.

Furthermore, as mentioned above, results presented in Heinrich et al., 2000 are contrary to those obtained in connection with the invention. The present invention describes a method directed at the identification of compounds capable of inhibiting constitutively activated c-kit. With this method, we were able to show that STI 571 is an inhibitor of c-kit wild but do not act on mutant activated c-kit such as the D816 mutant.

The general problem underlying the present invention is therefore to define a screening method allowing the identification and selection of non-toxic compounds capable of inhibiting c-kit, whether they are SCF-activated c-kit inhibitors, constitutively activated c-kit inhibitors or both.

Indolinone derivatives such as SU4984, SU6663, SU6577 and SU5614 have been tested for c-kit inhibition by Yongsheng Ma and B. Longley, Feb 2000; Indolinone derivatives inhibit constitutively activated KIT mutants and kill neoplastic mast cells, The Society For Investigative Dermatology, vol 114, no2, pages 392-394. It is shown in this publication that among the compound tested, only SU6,577 at 40 μM could substantially reduce receptor phosphorylation of the D816 mutant activated c-kit. This compound is also active on c-kit wild, but at a 40 μM concentration, the problem is that the activity of SU6577 on the D816 mutant might result from toxicity. A lack of specificity on c-kit versus other tyrosine kinases would render such a compound inadequate for therapeutic purposes.

In this regard, the method contemplated by the invention provides a second testing on IL-3 dependent cells cultured in presence of IL-3. Candidate compounds that are effective against activated c-kit are readily cross-checked for their specificity and toxicity.

Many different compounds have been described as tyrosine kinase inhibitors, for example, bis monocyclic, bicyclic or heterocyclic aryl compounds (WO 92/20642), vinylene-azaindole derivatives (WO 94/14808) and 1-cyclopropyl4-pyridyl-quinolones (U.S. Pat. No. 5,330,992), Styryl compounds (U.S. Pat. No. 5,217,999), styryl-substituted pyridyl compounds (U.S. Pat. No. 5,302,606), seleoindoles and selenides (WO 94/03427), tricyclic polyhydroxylic compounds (WO 92/21660) and benzylphosphonic acid compounds (WO 91/15495), pyrimidine derivatives (U.S. Pat. No. 5,521,184 and WO 99/03854), indolinone derivatives and pyrrol-substituted indolinones (U.S. Pat. No. 5,792,783, EP 934 931, U.S. Pat. Nos. 5,834,504, 5,883,116, 5,883,113,5, 886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. Nos. 3,772,295 and 4,343,940) and aryl and heteroaryl quinazoline (U.S. Pat. Nos. 5,721,237, 5,714,493, 5,710,158 and WO 95/15758).

None of these compounds, however, have been demonstrated to selectively inhibit activated c-kit, while being potent inhibitors of c-kit wild acting in the transphosphorylation domain and unable to promote death of IL-3 dependant cells cultured in presence of IL-3.

We further show here that specifically targeting the transphosphorylase or the juxtamembrane domain of c-kit is of interest. Indeed, mutations or deletions in these domains results in constitutively activated c-kit. For example, among compounds selected to be active on the D816 mutant as well as on SCF activated c-kit wild, some have been found in connection with the invention to be highly potent c-kit wild inhibitors.

DESCRIPTION

Therefore, the present invention relates to a screening method for identifying compounds that are selective and potent inhibitors of c-kit, which comprises a) bringing into contact (i) activated c-kit and (ii) at least one compound to be tested; under conditions allowing the components (i) and (ii) to form a complex, b) selecting compounds that inhibit activated c-kit, c) testing and selecting a subset of compounds identified in step b), which are unable to promote death of IL-3 dependant cells cultured in presence of IL-3.

In frame with the invention, the expression "activated c-kit" means a constitutively activated-mutant c-kit including at least one mutation selected from point mutations, deletions, insertions, but also modifications and alterations of the natural c-kit sequence (SEQ ID No 1). Such mutations, deletions, insertions, modifications and alterations can occur in the transphosphorylase domain, in the juxtamembrane domain as well as in any domain directly or indirectly responsible for c-kit activity. The expression "activated c-kit" also means herein SCF-activated c-kit. In a preferred embodiment, the activated-mutant c-kit in step a) has at least one mutation proximal to Y823, more particularly between amino acids 800 to 850 of SEQ ID No 1involved in c-kit autophosphorylation, notably the D816V, D816Y, D816F and D820G mutants. In another preferred embodiment, the activated-mutant c-kit in step a) has a deletion in the juxtamembrane domain of c-kit. Such a deletion is for example between codon 573 and 579 amino acids called c-kit d(573-579). The point mutation V559G proximal to the juxtamembrane domain c-kit is also of interest.

The screening method can further comprise the step consisting of testing and selecting a subset of compounds identified in step b) that are inhibitors of mutant activated c-kit (for example in the transphosphorylase domain), which are capable of inhibiting SCF-activated c-kit wild.

Alternatively, in step a) activated c-kit is SCF-activated c-kit wild.

A best mode for practicing this method consists of a testing at a concentration above 10 µM in step a). Relevant concentrations are for example 10, 15, 20, 25, 30, 35 or 40 µM.

In step c), IL-3 is preferably present in the culture media of IL-3 dependant cells at a concentration comprised between 0.5 and 10 ng/ml, preferably between 1 to 5 ng/ml. Examples of IL-3 dependant cells include but are not limited to cell lines naturally expressing and depending on c-kit for growth and survival. Among such cells, human mast cell lines can be established using the following procedures:

For example, normal human mast cells can be infected by retroviral vectors containing sequences coding for a mutant c-kit comprising the c-kit signal peptide and a TAG sequence allowing to differentiate mutant c-kits from c-kit wild expressed in hematopoetic cells by means of antibodies.

This technique is advantageous because it does not induce cellular mortality and the genetic transfer is stable and gives satisfactory yields (around 20%). Pure normal human mast cells can be routinely obtained by culturing precursor cells originating from blood obtained from human umbilical vein. In this regard, heparinated blood from umbilical vein is centrifuged on a Ficoll gradient so as to isolate mononucleated cells from other blood components. CD34+ precursor cells are then purified from the isolated cells mentioned above using the immunomagnetic selection system MACS (Mi ltenyi biotech). CD34+ cells are then cultured at 37° C. in 5% $CO_2$ atmosphere at a concentration of $10^5$ cells per ml in the medium MCCM (α-MEM supplemented with L-glutamine, penicillin, strleptomycin, $5\ 10^{-5}$ M β-mercaptoethanol, 20% veal foetal serum, 1% bovine albumin serum and 100 ng/ml recombinant human SCF. The medium is changed every 5 to 7 days. The percentage of mast cells present in the culture is assessed each week, using May-Grünwal Giemsa or Toluidine blue coloration. Anti-tryptase antibodies can also be used to detect mast cells in culture. After 10 weeks of culture, a pure cellular population of mast cells (<98%) is obtained.

It is possible using standard procedures to prepare vectors expressing c-kit for transfecting the cell lines established as mentioned above. The cDNA of human c-kit has been described in Yarden et al., (1987) EMBO J.6 (11), 3341-3351. The coding part of c-kit (3000 bp) can be amplified by PCR and cloned, using the following oligonucleotides:

5'AAGAAGAGATGGTACCTCGAGGGGTGA (SEQ ID No 2) sens CCC3'

5'CTGCTTCGCGGCCGCGTTAACTCTTCT (SEQ ID No 3) antisens CAACCA3'

The PCR products, digested with NotI and XhoI, has been inserted using T4 ligase in the pFlag-CMV vector (SIGMA), which vector is digested with NotI and XhoI and dephosphorylated using CIP (Biolabs). The pFlag-CMV-c-kit is used to transform bacterial clone XL1-blue. The transformation of clones is verified using the following primers:

5'AGCTCGTTTAGTGAACCGTC3' (SEQ ID No 4) sens,

5'GTCAGACAAAATGATGCAAC3' (SEQ ID No 5) antisens.

Directed mutagenesis is performed using relevant cassettes is performed with routine and common procedure known in the art.

The vector Migr-1 (ABC) can be used as a basis for constructing retroviral vectors used for transfecting mature mast cells. This vector is advantageous because it contains the sequence coding for GFP at the 3' and of an IRES. These features allow to select cells infected by the retrovirus using direct analysis with a fluorocytometer. As mentioned above, the N-terminal sequence of c-kit c-DNA can be modified to introduce a Flag sequence that will be useful to discriminating exogenous from endogenous c-kit.

Other IL-3 dependent cell lines that can be used include but are not limited to:
  BaF3 mouse cells expressing wild-type or mutated form of c-kit (in the juxtamembrane and in the catalytic sites) are described in Kitayama et al, (1996), Blood 88, 995-1004 and Tsujimura et al, (1999), Blood 93, 1319-1329.
  IC-2 mouse cells expressing either c-kit$^{WT}$ or c-kit$^{D814Y}$ are presented in Piao et al, (1996), Proc. Natl. Acad. Sci. USA 93, 14665-14669.
IL-3 independent cell lines are:
  HMC-1, a factor-independent cell line derived from a patient with mast cell leukemia, expresses a juxtamembrane mutant c-kit polypeptide that has constitutive kinase activity (Furitsu T et al, J Clin Invest. 1993;92: 1736-1744; Butterfield et al, Establishment of an immature mast cell line from a patient with mast cell leukemia. Leuk Res. 1988;12:345-355 and Nagata et al, Proc NatI Acad Sci U S A. 1995;92:10560-10564).
  P815 cell line (mastocytoma naturally expressing c-kit mutation at the 814 position) has been described in Tsujimura et al, (1994), Blood 83, 2619-2626.

The extent to which component (ii) inhibits activated c-kit can be measured in vitro or ex vivo. In case it is measured ex vivo, cell lines as prepared or listed above expressing an activated-mutant c-kit, which has at least one mutation proximal to Y823, more particularly between amino acids 800 to 850 of SEQ ID No1 involved in c-kit autophosphorylation, notably the D816V, D816Y, D816F and D820G mutants, are preferred.

In another preferred embodiment, the method further comprises the step consisting of testing and selecting compounds capable of inhibiting c-kit wild at concentration below 1 μM. This can be measured in vitro or ex vivo. Examples of cell lines expressing c-kit include but are not limited to: mast cells, transfected mast cells, HMC-1, BaF3, P815, and IC-2.

Therefore, compounds are identified and selected according to the method described above are potent, selective and non-toxic c-kit wild inhibitors. It is also worth noting that said inhibitors act on the transphosphorylation domain of c-kit wild.

In a further embodiment, the invention is directed to a screening method for identifying compounds that are selective and potent inhibitors of c-kit, which comprises:
  i) addition of chemical groups responsible for the inhibition of c-kit autophosphorylation to compounds identified by the method depicted above, wherein activated c-kit is SCF-activated c-kit wild,
  ii) testing and selecting a subset of compounds identified in step i), which inhibit activated-mutant c-kit as defined above, such as mutants in the transphophorylase domain.

Alternatively, the screening method according to the invention can be practiced in vitro In this regard, the inhibition of mutant-activated c-kit and/or c-kit wild can be measured using standard biochemical techniques such as immunoprecipitation and western blot. Preferably, the amount of c-kit phosphorylation is measured.

In a still further embodiment, the invention contemplates a screening method as described above for identifying potent and selective compounds that are inhibitors of c-kit comprising
  a) performing a proliferation assay with cells expressing a mutant c-kit (for example in the transphosphorylase domain), which mutant is a permanent activated c-kit, with a plurality of test compounds to identify a subset of candidate compounds targeting activated c-kit, each having an IC50<10 μM, by measuring the extent of cell death,
  b) performing a proliferation assay with cells expressing c-kit wild said subset of candidate compounds identified in step (a), said cells being IL-3 dependent cells cultured in presence of IL-3, to identify a subset of candidate compounds targeting specifically c-kit,
  c) performing a proliferation assay with cells expressing c-kit, with the subset of compounds identified in step b) and selecting a subset of candidate compounds targeting c-kit wild, each having an IC50<10 μM, preferably an IC50<1 μM, by measuring the extent of cell death.

Here, the extent of cell death can be measured by 3H thymidine incorporation, the trypan blue exclusion method or flow cytometry with propidium iodide. These are common techniques routinely practiced in the art.

Compounds that are intended to be screened can be tyrosine kinase inhibitors. Many different compounds have been described as tyrosine kinase inhibitors, for example, bis monocyclic, bicyclic or heterocyclic aryl compounds (WO 92/20642), vinylene-azaindole derivatives (WO 94/14808) and 1-cyclop roppyl4-pyridyl-quinolones (U.S. Pat. No. 5,330,992), Styryl compounds (U.S. Pat. No. 5,217,999), styryl-substituted pyridyl compounds (U.S. Pat. No. 5,302, 606), seleoindoles and selenides (WO 94/03427), tricyclic polyhydroxylic compounds (WO 92/21660) and benzylphosphonic acid compounds (WO 91/15495).

Therefore, the invention relates to a screening method as defined above, wherein said compounds are selected from the group consisting of indolinone, pyrimidine derivatives, pyrrolopyrimidine derivatives, quinazoline derivatives, quinoxaline derivatives, pyrazoles derivatives, bis monocyclic, bicyclic or heterocyclic aryl compounds, vinylene-azaindole derivatives and pyridyl-quinolones derivatives, styryl compounds, styryl-substituted pyridyl compounds, , seleoindoles, selenides, tricyclic polyhydroxylic compounds and benzylphosphonic acid compounds.

Among preferred compounds to be tested according to the method of the invention, it is of interest to focus on pyrimidine derivatives such as N-phenyl-2-pyrimidine-amine derivatives of formula I:

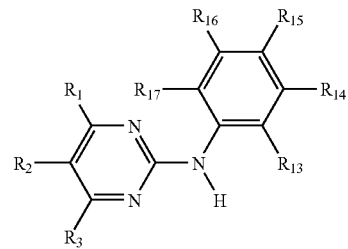

wherein the R1, R2, R3, R13 to R17 groups have the meanings depicted in EP 564 409 B1, incorporated herein in the description.

Preferably, the N-phenyl-2-pyrimidine-amine derivative is selected from the compounds corresponding to formula II:

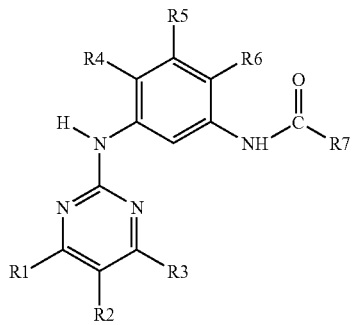

Wherein R1, R2 and R3 are independently chosen from H, F, Cl, Br, I, a C1-C5 alkyl or a cyclic or heterocyclic group, especially a pyridyl group;

R4, R5 and R6 are independently chosen from H, F, Cl, Br, I, a C1-C5 alkyl, especially a methyl group;

and R7 is a phenyl group bearing at least one substituent, which in turn possesses at least one basic site, such as an amino function.

For example R7 can be

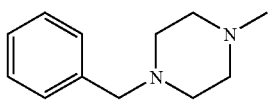

Among these compounds, the preferred are defined as follows:

R1 is a heterocyclic group, especially a pyridyl group,
R2 and R3 are H,
R4 is a C1-C3 alkyl, especially a methyl group,
R5 and R6 are H,
and R7 is a phenyl group bearing at least one substituent, which in turn possesses at least one basic site, such as an amino function, for example the group:

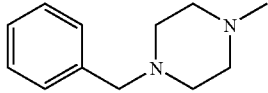

The preparation of such compounds is described in example 21 of EP 564 409.

Alternatively, the screening may be performed with indolinone derivatives and pyrrol-substituted indolinones (U.S. Pat. No. 5,792,783, EP 934 931, U.S. Pat. No. 5,834,504), U.S. Pat. Nos. 5,883,116, 5,883,113, 5,886,020, WO 96/40116 and WO 00/38519), as well as bis monocyclic, bicyclic aryl and heteroaryl compounds (EP 584 222, U.S. Pat. No. 5,656,643 and WO 92/20642); quinazoline derivatives (EP 602 851, EP 520 722, U.S. Pat. Nos. 3,772,295 and 4,343,940), 4-amino-substituted quinazolines (U.S. Pat. No. 3,470,182), 4-thienyl-2-(1H)-quinazolones, 6,7-dialkoxyquinazolines (U.S. Pat. No. 3,800,039), aryl and heteroaryl quinazoline (U.S. Pat. Nos. 5,721,237, 5,714,493, 5,710,158 and WO 95/15758), 4-anilinoquinazoline compounds (U.S. Pat. No. 4,464,375), and 4-thienyl-2-(1H)-quinazolones (U.S. Pat. No. 3,551,427).

So, preferably, the invention also relates to a screening method as defined above, wherein said compounds are
  pyrimidine derivatives, more particularly N-phenyl-2-pyrimidine-amine derivatives.
  indolinone derivatives, more particularly pyrrol-substituted indolinones,
  monocyclic, bicyclic aryl and heteroaryl compounds,
  or quinazoline derivatives.

The invention is also directed to a compound obtainable by the method as depicted above, wherein said compound is a selective and potent inhibitor of activated c-kit, a potent inhibitors of c-kit wild acting in the transphosphorylation domain and is unable to promote death of IL-3 dependant cells cultured in presence of IL-3.

The invention also embraces the use of said compound to manufacture a medicament.

Utility of the invention will further ensue from the detailed description of molecular mechanisms of signal transduction via c-kit and mutated c-kit that are implicated in numerous diseases.

Signal Transduction Induced by Activation of Normaal C-Kit.

SCF is an essential growth factor in hematopoiesis since it synergizes with almost all the hematopoietic growth factors, except M-CSF, to induce in vitro hematopoiesis [17]. This factor is produced by bone marrow stromal cells, and acts through interaction with its receptor, c-kit [18]. As previously noticed, the c-kit receptor is a glycoprotein of 145 kDa and belongs to the type II tyrosine kinase subfamily, characterized by the presence of five lg-like domains in the extracellular part of the molecule and by an interkinase sequence that splits the intracytoplasmic domain into the adenosine triphosphate (ATP)-binding domain and the phosphotransferase domain [1]. C-kit is strongly expressed by CFU-GEMM, BFU-E and by progenitors and mature cells of the mast cell lineage [19].

Ligand binding to c-kit results in activation of the catalytic function, resulting in autophosphorylation of tyrosine residues of the cytoplasmic domain. These phosphotyrosine residues become docking sites for various cytoplasmic signaling molecules containing SH2 domain. C-kit activates canonical signal transduction pathways common to many growth factor receptors, including those depending on P13-kinase, ras and JAK2. Molecules known to associate with c-kit in vivo or in vitro include p85 subunit of P13-kinase, multiple Src family members, Lyn and Fyn, Vav, Grb2, SHP-1, SHP-2, PKC, MATK (CHK) and Socs1, while there are divergent data concerning PLC-γ, GTPase activating Protein of ras (GAP) and JAK2. Additional molecules are activated or phosphorylated in response to c-kit activation: Shc, Tec, Vav GDP/GTP exchange factor, raf-1, MAPK, Akt, CRKL, p120 Cbl, and Doc. Recent studies performed in various cell systems have yielded divergent results regarding the substrates that associate with and are phosphorylated by c-kit. These discrepancies might reflect either differences in experimental methods or functionally relevant variations in substrate expression profiles of individual cell types, which could be the basis of distinct signals and cell type specific responses mediated by the same ligand/receptor system. For these reasons, we choose to describe the data obtained regarding c-kit signaling in various cellular contexts.

The first initiator of signalization is the ligand induced-dimerization of c-kit, which induces intrinsic tyrosine kinase activity of c-kit, resulting in transphosphorylation at critical tyrosine residues [10]. Moreover, in response to ligand stimulation, c-kit appears to be phosphorylated on serine residues by PKC, which inhibits c-kit autophosphorylation [20].

One of the most efficient associations with c-kit, observed in various cell types, is contracted by SH2 domain of p85 subunit of P13-kinase [21, 22] via the phosphorylated tyrosine residue 719 of murine c-kit or tyrosine 721 of human c-kit [23].

C-kit signalisation has been studied in human hematopoietic cells, mainly in M07e and CMK, two megakaryocytic cell lines (Table 1 below).

TABLE 1

Molecules interacting with the intracellular portion of the human c-kit and/or activated in response to SCF.

| Molecules | Human cells | References |
|---|---|---|
| Akt | 293, U2OS, BHX21, HeLa | [82] |
| c-Cbl | MO7e, TF-1 | [79, 80] |
| CRKL | MO7e | [81] |
| Doc | MO7e | [86] |
| p125 Fak | TF-1 | [94] |
| Fyn | MO7e | [127] |
| Grap | MO7e, TF-1, K562 | [78] |
| Jak2 | MO7e, TF-1 | [87, 88] |
| Lyn | MO7e, Normal progenitors | [128] |
| MAPK | melano 501 mel | [93] |
| MATK (CHK) | CMK | [84, 127] |
| P13-K | 293, U2OS, BHX21, HeLa | [82, 91] |
| PLC-γ | MO7e | [99] |
| Raf1 | MO7e | [77] |
| Ras | MO7e | [77] |
| SHP-1 | MO7e | [97] |
| SHP2 (Syp) | MO7e | [77] |
| Tec | MO7e | [83] |
| Vav | MO7e, TF-1 | [85] |

In these cells, SCF induces activation and/or recruitment of major kinases such as P13-kinase, Src kinases (Fyn and Lyn) and JAK2, and various adaptators molecules, Grb2, Grap, Vav, CRKL via their SH2 domain. These events result in formation of various molecular associations via SH2, SH3 or PH domains, which in turn start activation of different pathways. Ras pathway was showed to be activated in response to SCF stimulation, leading to interaction between Ras and Raf-1, thus initiating MAPKinase cascade [24]. Indeed, Grap, an adaptator molecule, interacts with. ligand-activated c-kit through its SH2 domain and is associated with a ras guanine nucleotide exchange factor, mSos1, through its SH3 domain, coupling signals from receptor and cytoplasmic tyrosine kinase to the ras signaling pathway [25]. Another adaptator molecule related to Grap, Grb2, interacting via its SH2 domain with a phosphorylated tyrosine residue of c-kit, may recruit c-Cb1 and Shc [26, 27]. After activation, kinase may either play the role of adaptator molecule such as P13-kinase interacting with c-Cbl and CRKL [28], or the role of kinase such as P13-kinase phosphorylating Akt [29]. In few cases, interaction and/or activation is described without connection with any known signaling pathway. This is the case for Tee [30], MATK [31], Vav [32] and Doc [33]. Unexpectedly, JAK-STAT pathway is poorly described during c-kit activation. JAK2, a cytosolic tyrosine kinase essential for non tyrosine kinase cytokine receptor superfamily signaling, has been described physically associated with c-kit, prior to ligand activation, and phosphorylated on tyrosine residues in response to SCF [34-36], or not associated with c-kit [30]. In addition, SCF activates cytosolic transcription factors like STAT1 in MO7e cell line [37].

C-kit signalisation has been also examined in various non hematopoietic human cell lines. Blume-Jensen et al. demonstrated that SCF induced activation of Akt and mediated phosphorylation of Serine residue 136 of Bad in a P13-kinase-dependent manner [29]. In vitro experiments performed on embryonic fibroblasts indicate that P13-kinase and PLC-γ compete for association with tyrosine residue 721 of human c-kit, with p85/P13-kinase exhibiting higher affinity [38]. In H526 cell line (Small cell lung carcinoma, SCLC), SCF induced activation of Src-kinase, Lck, and its interaction with the juxtamembrane domain of c-kit [39]. In 501 mel, a human melanoma cell line, Hemesath et al. described that SCF stimulation resulted in activation of MAPK which, in turn, phosphorylated transcription factor microphtalm ia (Mi), upregu lati ng Mi transactivation via interaction with p300/CBP [40].

Interestingly, interconnection between c-kit and integrin signaling pathways was observed in TF-1 cell line [94]. SCF induces spreading of fibronectin-adherent TF-1 cells and enhances tyrosine phosphorylation of pp125 FAK in a dose-dependent manner, when compared to the level of tyrosine phosphorylation of pp125 FAK in the absence of SCF. These effects depend on a worthmannin-, integrin activation-sensitive pathways.

Regarding c-kit deactivation, two main pathways have been described in different cellular contexts. In hematopoietic cells, one pathway involves SHP-1, a tyrosine phosphatase, interacting with c-kit probably at 569 tyrosine phosphorylated residue, which down-regulates tyrosine residue phosphorylation state of c-kit. [42-45]. The role of phosphatase SHP-2 (Syp) is less clear. It has been shown that SHP-2 associated with activated c-kit in MO7e cell line via its SH2 domain, became phosphorylated and complexed with Grb2 [24]. This connection to Grb2 could lead to ras/MAP-kinase pathway activation and to cell proliferation. By contrast, it has been shown, in BA/F3 cells expressing c-kit, that SHP-2 association to c-kit Y567F is markedly reduced. In this case, an hyperproliferative response to SCF was observed, suggesting that SHP-2 downregulates SCF-induced proliferation [45].

Activation and deactivation of human c-kit have been also studied in porcine endothelial cells (PAE) (Table 5). Activation of P13-kinase, PLC-γ and Raf/MAPKinase cascade was described in response to SCF in PAE cells transfected with human c-kit [46]. In these cells, a first negative feedback loop is the P13-K, PLD and PKC pathway which leads to phosphorylation at 741 and 746 serine residues of c-kit [47]. A second deactivation pathway is P13-kinase-induced PLD activation and phosphatidyicholine (PtdCho)-specific phospholipase D activation, (PtdCho)-PLD, that generated phosphatidic acid (PtdH), metabolized into diacylglycerol (DAG), an activator of PKC and a precursor of arachidonic acid (D4Ach) [48]. These authors -also showed that SCF induced PLA2 activation, a second pathway generating D4Ach.

In murine bone marrow-derived mast cells (BMMC), it has been demonstrated that SCF induces i) P13-kinase activation, which in turn stimulates Rac-1 and Jnk pathway [49] and ii) binding and phosphorylation of Src kinases Fyn on tyrosine 567 [49] and Lyn [50]. In rat mast cells isolated from the peritoneal cavity, Koike et al. have shown that SCF induced PLD activation and subsequent release of D4Ach through the protein tyrosine kinase pathway and without activation of the phosphoinositide-specitic PLC-γ [51, 52]. In these cells, Nagai et al. have shown the involvement of P13-kinase, protein tyrosine kinase (PTK) and myosin light chain kinase in SCF induced histamine release [53]. Regarding c-kit deactivation in murine cells, another way to decrease SCF signal is the down-modulation of c-kit expression. Yee et al. and Miyazawa et al. have shown that c-kit internalization and ubiquitination is dependent on intact kinase activity of c-kit [54, 55]. In BMMC, c-kit activates PLC-γ resulting in the hydrolysis of P14,5 diP into DAG and inositol-1,4,5 triP inducing mobilization of intracelidlar $Ca^{++}$ [56]. This calcium influx seems to be critical for c-kit internalization. Moreover, in the absence of P13-kinase activation, the c-kit receptor internalizes but remains localized near the inner side of the plasma membrane. Of note, c-kit internalization is completely prevented when both P13-kinase and $Ca^{++}$ influx are inhibited [56]. A novel mediator of downregulation of c-kit-dependent mitogenesis could be Socs-1 (Suppressor of cytokine signaling) [57]. SCF induces synthesis of Socs-1, that binds to c-kit via its SH2 domain. The mechanism is of Socs-1 activity seems to involve its interaction with Grb2 and the negative regulatory N-terminus of Vav [58].

Molecular Dysfunctions Related to C-Kit Mutations c-kit mutations found in humans affect phosphotransferase domain near Y823 site of autophosphorylation. However, studies concerning molecular dysfunctions of c-kit mutants revealed that mutations alter various aspects of c-kit metabolism: dimerization, signaling, enzyme expression and internalization.

C-Kit Receptor Dimerization

The c-kit receptor dimerization is a key event in signal transduction, and takes place before tyrosine phosphorylation. A sequential model of c-kit activation is proposed by Blechman et al. [58]. Monovalent SCF binding exposes a putative receptor site that facilitates rapid dimerization of the receptor, further stabilized by binding of the second arm of the dimeric SCF molecule. Ligand binding site seems to be confined to the three N-terminal Ig-like domains, and dimer formation seems to be mediated by the fourth Ig-like domain [10, 58].

Thus, modifications of c-kit can alter either the dimerization domain or the transduction domain of this receptor. Tsujimura et al. [59] and Kitayama et al. [60] have performed cross-linking analysis of various c-kit receptors, wild type and mutated variants, to determine whether the constitutively activated c-kit leads to receptor dimerization or not, in the absence of SCF. They have respectively studied four forms of c-kit:c-kit$^{WT}$, c-kit$^{d(573-579)}$ (c-kit with a deletion from codon 573 to 579), c-kit$^{V559G}$ or c-kit$^{D814Y}$ that were introduced in Ba/F3 cells. SCF induces tyrosine phosphorylation of c-kit$^{WT}$ that is detected at an approximate molecular weight of 330 kDa, representing a complex containing cross-linked homodimer of c-kit$^{WT}$ and SCF. After treatment with SCF, the phosphorylated forns of c-kit$^{d(573-579)}$ and c-kit$^{V559G}$ are detected with a molecular mass of 330 kDa, as for c-kit$^{WT}$. In the absence of SCF, an abundant tyrosine phosphorylation of c-kit$^{d(573-579)}$ and c-kit$^{V559G}$ is observed and corresponds to a 290 kDa cross-linked homodimer of the c-kit mutant. By contrast, in the absence of SCF, constitutively phosphorylated c-kit$^{D814V}$ is scarcely detectable as a 290 kDa dimeric form, whereas a 330 kDa that represents a cross-linked complex, containing homodimer of c-kit$^{D814V}$ and SCF, is observed after stimulation with SCF. These data suggest that an activating deletion, such as c-kit$^{d(573-579)}$, or an activating mutation, such as the c-kit$^{V559G}$, that take place in the juxtamembrane domain are able to induce a constitutive dimerization of c-kit in the absence of SCF stimulation, whereas an activating mutation at the catalytic kinase domain (c-kit$^{D814V}$) causes constitutive activation of c-kit without dimerization.

Nevertheless, Tsujimura et al. have reported contrasting data concerning the mechanism of c-kit$^{D814V}$ or c-kit$^{D814Y}$ constitutive activation [61]. Indeed, they found that a truncated form of this variant receptor, devoid of extracellular domain, was constitutively activated and capable of conferring factor-independent growth to inurine IL-3-dependent Ba/F3 cells, whereas equivalent truncation of wild type c-kit was unable to-do so, suggesting that extracellular domain is not involved in the constitutive activation of c-kit$^{D814Y}$ or c-kit$^{D814V}$. Moreover, these authors presented data indicating that c-kit$^{D814V}$ may not function as a monomeric form. They observed that extracellular domain-truncated c-kit$^{D814V}$ coimmunoprecipitated with full length wild-type receptor or c-kit$^{W42}$, a dominant negative receptor. These authors proposed that self-association of c-kit$^{D814Y}$ or c-kit$^{D814V}$ might result from the mutation itself by creating a novel receptor self-association domain.

Signaling Alterations

Concerning c-kit$^{D814Y}$, Piao et al. [62] have investigated the mechanism of oncogenic activation by this mutation in the murine mast cell line IC2, expressing either c-kit$^{WT}$ or c-kit$^{D814Y}$.

In this cell line, expression of c-kit$^{D814Y}$ altered c-kit signaling when compared to c-kit$^{WT}$ [62]. C-kit$^{D814Y}$ mutation introduced changes in the substrate recognition of c-kit, as observed in the pattern of receptor autophosphorylation sites, the pattern of tyrosine phosphorylated proteins and the selectivity of the mutated receptor for synthetic peptidic substrates. This is relevant to the fact that this mutation changes a residue conserved in the receptor tyrosine kinase family (RTK) into a residue conserved in the non receptor tyrosine kinase family (NRTK), including c-Abl. Then, this mutation might alter receptor conformation to favor interaction with group I SH2 domain, relevant substrates for NRTK [63, 64]. One novel substrate could be the 130 kDa protein detected by these authors. Moreover, given the fact that SHP-1 desactivates c-kit, c-kit$^{D814Y}$ mutation might alter one way of c-kit deactivation by increasing the rate of SHP-1 Ub-mediated proteolysis, since SHP-1 is absent in c-kit$^{D814Y}$ expressing cells. In fact, a peptide inhibitor of the proteolytic pathway, LLnL, stabilizes SHP-1 and prevents its degradation. So, two main arguments could explain the expansion of IC2/c-kit$^{D814Y}$ cells in the absence of any growth factors: the constitutive kinase activity of the mutant c-kit$^{D814Y}$ and the enhanced degradation of SHP-1. Whatsoever, the authors have not presented data suggesting that c-kit$^{D814Y}$ activation is more prolonged than that of c-kit$^{WT}$. To argue the fact that the mutation c-kit$^{D814Y}$ might alter the fidelity of c-kit signaling, one could notice the parallel between this mutation and the mutation M918T of Ret, found in 95% of multiple endocrine neoplasia type 2B (NEM 2B) [65]. Ret is another tyrosine kinase receptor belonging to PDGF receptor family in which M918 is highly conserved.[66, 67]. Interestingly, in other tyrosine kinase receptor family, there is a threonine at equivalent codon, suggesting that M918T mutation induces alteration in substrate affinity or affinity for new substrate.

Enzymatic Functions and c-Kit Mutations

SHP-1 expression is different in IC2/c-kit$^{WT}$ and IC2/c-kit$^{D814Y}$ cells, and this is also the case for other proteins like MMCP-4 and MMCP-6, that are proteases present in the granules of murine mast cells and differentially expressed at various stages of mast cell maturation. Indeed, MMCP-6 transcripts are expressed at low level in IC2/c-kit$^{WT}$ cells in the presence of exogenous SCF, and this level increases as the result of c-kit$^{D814Y}$ expression. MMCP-4 transcripts are not detectable by RT-PCR in IC2/c-kit$^{WT}$ cells, but are abundantly expressed in IC2/c-kit$^{D814Y}$ cells. The differences observed between the wild form and the mutant suggest that the signals transduced by c-kit$^{WT}$ stimulated by SCF and by c-kit$^{D814Y}$ are not equivalent : the mutation c-kit$^{D814Y}$ alters not only the proliferation of mast cells but also their stage of maturation.

Receptor Internalization and c-Kit Mutations

Downregulation of the internalization signal can take part in the prolonged activation of c-kit, since internalization is known to serve as an attenuation mechanism for receptor signaling. In fact, studies on the kinetics of degradation of c-kit receptor showed that without SCF, the surface c-kit$^{d(573-579)}$ decreases barely, whereas when FMA3 cells are incubated with SCF, the surface c-kit$^{d(573-579)}$ decreases remarkably. By contrast, the activated c-kit$^{D814V}$ receptor is continuously degraded, even in the absence of SCF [68]. Since calcium metabolism and P13-kinase activity were described as mediators of c-kit internalization [54-56], it will be interesting to study these pathways in cells expressing c-kit$^{d(573-579)}$ c-kit$^{V559G}$, or c-kit$^{D814V}$.

EXAMPLE 1

Methodology/Experimental Approaches

First step: cellular proliferation to select molecules which are able to slowdown or stop cellular growth induced by c-kit activation. Here, SCF activated c-kit is used. Then, the effect of these molecules is analyzed by biochemistry techniques (immuno precipitations and western-blots), so that to determine if the inhibitor acts directly on the receptor c-kit or on other proteins, which are mediators of Kit signals. In a second step, a subset of molecules identified is selected in a cellular test on IL-3 dependant cells cultured in presence of IL-3. molecules that are not toxic are identified as potent specific c-kit inhibitors for a use in therapy.

EXAMPLE 2

Cellular Models

Two types of cell lines carrying wild or mutated forms of c-kit are available lines derived from mastocytomes and the Ba/F3 cell model (cells depending on IL-3). In the Ba/F3 cells, the expression of c-kit removes the dependence vis-a-vis IL-3. Consequently, cDNA of wild or mutated murine c-kit has been introduced and these cells proliferate either in presence of SCF in case of c-kit wild or in absence of any growth factor in case of activated mutant c-kit.
  Preparation of cell lines
  Ba/F3-Kit: Ba/F3 cells in which Kit gene, mutated or wild, has been introduced. They proliferate either in presence of Kit ligand (SCF) or in presence of IL-3.
  Juxtamembrane Mutations
  Ba/F3-KitΔ27 (transfected juxtamembrane mutation—identified at the Laboratory)
  Ba/F3-KitG559 (transfected juxtamembrane mutation)
  FMA3 (deletion 7aa. juxtamembrane identified in a mouse mastocytome)
  Mutation in the Kinase Domain (Residue 814)
  IC2 (murine mast cell line which does not express endogenous c-kit) transfected with the 814 mutated c-kit
  P815 (murine mastocytoma cell line expressing an endogenous c-kit carrying the 814V mutation).

EXAMPLE 3

Study of STI 571 on c-Kit Wild and Mutant Activated c-Kit

The inhibitor of oncogene BCR-ABL, STI 571, is also an inhibitor of PDGF receptor, which is related to c-kit. Consequently, the STI 571 has been tested on Kit.
  2.1 Effect of STI 571 on Cellular Proliferation Induced by c-Kit (FIG. 1).
  For these experiments, IL-3 is used as a control to determine toxic doses of the inhibitor. At doses inferior to toxicity level (<10 µM), we found that STI 571 inhibits totally the proliferation depending on c-kit in case of c-kit wild and of juxtamembrane mutations (Δ27, FMA3) but not the proliferation of cells carrying 814 mutation (IC2 and P815).
  2.2 Effect of STI 571 on activated c-Kit
  The first step of c-kit activation consists of receptor phosphorylation on tyrosine residues. Thus, the phosphorylation state is a measure of receptor activation. By using specific antibodies, c-kit has been isolated by immunoprecipitation and c-kit phosphorylation has been determined using common procedures. The STI 571 considerably reduces the phosphorylation of c-kit wild and of c-kit bearing juxtamembrane mutations. On the contrary, the phosphorylation of the 814 mutant c-kit is not reduced by the STI 571.
  Conclusion: STI 571 is a new inhibitor very efficient on c-kit wild and on juxtamembrane activating mutations of Kit but it does not inhibit the 814 mutant c-kit.

EXAMPLE 4

Study of 37 New Potential c-Kit Inhibitors

We have tested 37 compounds that are indolinone derivatives in different cell lines and successive screening to select interesting inhibitors.
  Method: select the compounds which are effectively c-kit inhibitors (Table 1) Each compound has been tested at a high dose (10 µM) on cell expressing
  c-kit carrying the 814 mutation
  SCF activated c-kit wild
  control cells cultivated in IL-3.
  Cells expressing c-kit carrying one of the juxtamembrane mutations (Δ27) were also used as a control.
  Results: 21 compounds inhibit the 814 mutant c-kit: 6, 9, 10, 11, 14, 16, 17, 18, 19, 20, 21, 26, 28, 29, 30, 31, 32, 33, 34, 35 and 36.
    some compounds have poor inhibiting abilities on SCF activated c-kit: 7, 12, 13, 24, 25 and 27): these compounds are consequently eliminated. The 21 compounds above are selected as being also active on SCF activated c-kit.
    10 compounds are efficient on c-kit wild but not on 814 mutated c-kit: 1, 2, 3, 4, 5, 8, 15, 22, 23 and 37 (they supposedly don't act on the transphosphorylation domain of c-kit).
    Second selection: selection within the 21 compounds of those who are active at lower doses
    The effect of the 21 inhibitors has been tested at decreasing concentrations (10-10$^{-1}$-10$^{-2}$ µM) in order to reveal compounds that are able at 1 µM to inhibit proliferation of the IC2 D814V line while preserving response to another stimulus (IL-3, toxicity control). Nine inhibitors have been selected on the remaining 21 presenting interesting proliferation profiles: 10, 11, 14, 16, 17, 18, 19, 31 and 35.
    Third selection: identification of the most efficient compounds (the most specific of 814 mutation)
    The nine compounds selected have been tested at narrower doses: between 0.1 and 1 µM. At this stage, the three most efficient compounds at lower doses have been selected (≦0.6 µM): 11, 14 and 35.
    Compound no 11 is a good candidate for therapeutic uses since it shows a weak activity on the IL-3 dependant cell line indicated that it is less toxic.

TABLE 2

Proliferation test in presence of compounds at a dose of 10 μM

| Compound No | Ba/F3 Kit 1L3 | Ba/F3 Kit SCF | Ba/F3 Δ27 | IC2 D814V |
|---|---|---|---|---|
| 1 | − | + | −− | −− |
| 2 | − | ++ | ++ | − |
| 3 | −− | ++ | ++ | −− |
| 4 | +/− | ++ | +/− | +/− |
| 5 | − | + | − | +/− |
| 6 | − | ++ | ++ | +/− |
| 7 | −− | +/− | − | −− |
| 8 | −− | ++ | + | −− |
| 9 | ++ | ++ | ++ | ++ |
| 10 | ++ | ++ | ++ | ++ |
| 11 | + | ++ | ++ | ++ |
| 12 | −− | −− | −− | −− |
| 13 | −− | +/− | −− | −− |
| 14 | ++ | ++ | ++ | ++ |
| 15 | − | ++ | ++ | − |
| 16 | ++ | ++ | ++ | ++ |
| 17 | ++ | ++ | ++ | ++ |
| 18 | ++ | ++ | ++ | ++ |
| 19 | ++ | ++ | ++ | ++ |
| 20 | ++ | ++ | ++ | ++ |
| 21 | ++ | ++ | ++ | ++ |
| 22 | −− | + | ++ | − |
| 23 | −− | ++ | + | −− |
| 24 | −− | − | −− | −− |
| 25 | −− | +/− | −− | −− |
| 26 | ++ | ++ | ++ | + |
| 27 | −− | −− | −− | −− |
| 28 | ++ | ++ | ++ | ++ |
| 29 | ++ | ++ | ++ | ++ |
| 30 | ++ | ++ | ++ | ++ |
| 31 | ++ | ++ | ++ | ++ |
| 32 | ++ | ++ | ++ | ++ |
| 33 | ++ | ++ | ++ | ++ |
| 34 | ++ | ++ | ++ | ++ |
| 35 | ++ | ++ | ++ | ++ |
| 36 | ++ | ++ | ++ | ++ |
| 37 | +/− | ++ | ++ | − |

Table set up according to CPM (Counts Per Minutes) percentage obtained after proliferation in absence of inhibitors as 100% (% CPM>80=−−/50<% CPM<80=−/20<% CPM <50=+/5<% CPM<20=+/%-CPM<5=++). All experiments were done in triplicate.

FIG. 1 presents a test of specificity versus toxicity (kit D814 versus kit +IL3) at low concentrations. These results show that compounds No 11 is non toxic at concentration efficient to inhibit SCF and mutant activated c-kit.

REFERENCES

1. Yarden, Y., Kuang, W., Yang-Feng, T., Coussens, L., Munemitsu, S., Dull, T., Chen, E., Schlessinger, J., Francke, U., Ullrich, A. (1987) Human proto-oncogene c-kit: a new cell surface receptor tyrosine kinase for an unidentified ligand. EMBO J. 6, 3341-3351.
2. d'Auriol, L., Mattei, M.G., Andre, C., Galibert, F. (1988) Localization of the human c-kit protooncogene on the q11-q12 region of chromosome 4. Hum. Genet. 78, 374-376.
3. Matous, J., Langley, K., Kaushansky, K. (1996) Structure-function relationships of stem cell factor: an analysis based on a series of human-murine stem cell factor chimera and the mapping of a neutralizing monoclonal antibody. Blood 88, 437-444.
4. McNiece, I. K., Briddell, R. A. (1995) Stem cell factor. J. Leukoc. Biol. 58, 14-22.
5. Zsebo, K., Williams, D., Geissler, E., Broudy, V., Martin, F., Atkins, H., Hsu, R., Birkett, N., Okino, K., Murdock, D., et, a. (1990) Stem cell factor is encoded at the S1 locus of the mouse and is the ligand for the c-kit tyrosine kinase receptor. Cell 63, 213-224.
6. Flanagan, J. G., Leder, P. (1990) The kit ligand: a cell surface molecule altered in steel mutant fibroblasts. Cell 63, 185-194.
7. Geissler, E. N., Liao, M., Brook, J. D., Martin, F. H., Zsebo, K. M., Housman, D. E., Galli, S. J. (1991) Stem cell factor (SCF), a novel hematopoietic growth factor and ligand for c-kit tyrosine kinase receptor, maps on human chromosome 12 between 12q14.3 and 12qter. Somat. Cell. Mol. Genet. 17, 207-214.
8. Anderson, D. M., Lyman, S. D., Baird, A., Wignall, J. M., Eisenman, J., Rauch, C., March, C. J., Boswell, H. S., Gimpel, S. D., Cosman, D., et al. (1990) Molecular cloning of mast cell growth factor, a hematopoietin that is active in both membrane bound and soluble forms. Cell 63, 235-243.
9. Lev, S., Givol, D., Yarden, Y. (1991) A specific combination of substrates is involved in signal transduction by the kit-encoded receptor. EMBO J. 10, 647-654.
10. Blechman, J. M., Lev, S., Barg, J., Eisenstein, M., Vaks, B., Vogel, Z., Givol, D., Yarden, Y. (1995) The fourth immunoglobulin domain of the stem cell factor receptor couples ligand binding to signal transduction. Cell 80, 103-113.
11. Besmer, P., Murphy, J. E., George, P. C., Qiu, F. H., Bergold, P. J., Lederman, L., Snyder, H. W., Jr., Brodeur, D., Zuckerman, E. E., Hardy, W. D. (1986) A new acute transforming feline retrovirus and relationship of its oncogene v-kit with the protein kinase gene family. Nature 320, 415-421.
12. Krystal, G. W., Hines, S. J., Organ, C. P. (1996) Autocrine growth of small cell lung cancer mediated by coexpression of c-kit and stem cell factor. Cancer Res. 56, 370-376.
13. Bellone, G., Silvestri, S., Artusio, E., Tibaudi, D., Turletti, A., Geuna, M., Giachino, C., Valente, G., Emanuelli, G., Rodeck, U. (1997) Growth stimulation of colorectal carcinoma cells via the c-kit receptor is inhibited by TGF-beta 1. J. Cell. Physiol. 172, 1-11.
14. Hines, S. J., Organ, C., Komstein, M. J., Krystal, G. W. (1995) Coexpression of the c-kit and stem cell factor genes in breast carcinomas. Cell Growth Differ. 6, 769-779.
15. Inoue, M., Kyo, S., Fujita, M., Enomoto, T., Kondoh, G. (1994) Coexpression of the c-kit receptor and the stem cell factor in gynecological tumors. Cancer Res. 54, 3049-3053.
16. Cohen, P. S., Chan, J. P., Lipkunskaya, M., Biedler, J. L., Seeger, R. C. (1994) Expression of stem cell factor and c-kit in human neurbblastoma. The Children's Cancer Group. Blood 84, 3465-3472.
17. Metcalf, D. (1993) The cellular basis for enhancement interactions between stem cell factor and the colony stimulating factors. Stem Cells (Dayt) II Suppl 2, 1-11.
18. Ratajczak, M. Z., Luger, S. M., DeRiel, K., Abrahm, J., Calabretta, B., Gerwirtz, A. M. (1992) Role of the KIT protooncogene in normal and malignant human hematopoiesis. Proc. Nati. Acad. Sci. USA 89, 1710-1714.
19. Katayama, N., Shih, J. P., Nishikawa, S., Kina, T., Clark, S. C., Ogawa, M. (1993) Stage-specific expression of c-kit protein by murine hematopoietic progenitors. Blood 82, 2353-2360.
20. Blume-Jensen, P., Siegbahn, A., Stabel, S., Heldin, C. H., Ronnstrand, L. (1993) Increased Kit/SCF receptor induced mitogenicity but abolished cell motility after inhibition of protein kinase C. EMBO J. 12, 4199-4209.
21. Lev, S., Givol, D., Yarden, Y. (1992) Interkinase domain of kit contains the binding site for phosphatidylinositol 3' kinase. Proc. Natl. Acad. Sci. USA 89, 678-682.
22. Rottapel, R., Reedijk, M., Williams, D. E, Lyman, S. D., Anderson, D. M., Pawson, T., Bernstein, A. (1991) The Steel/W transduction pathway: kit autophosphorylation and its association with a unique subset of cytoplasmic signaling proteins is induced by the Steel factor. Mol. Cell. Biol. 11, 3043-3051.
23. Serve, H., Hsu, Y. C., Besmer, P. (1994) Tyrosine residue 719 of the c-kit receptor is essential for binding of the P85 subunit of phosphatidylinositol (PI) 3-kinase and for c-kit-associated P13-kinase activity in COS-1 cells. J. Biol. Chem. 269, 6026-6030.
24. Tauchi, T., Feng, G. S., Marshall, M. S., Shen, R., Mantel, C., Pawson, T., Broxmeyer, H. E. (1994) The ubiquitously expressed Syp phosphatase interacts with c-kit and Grb2 in hematopoietic cells. J. Biol. Chem. 269,25206-25211.
25. Feng, G. S., Ouyang, Y. B., Hu, D. P., Shi, Z. Q., Gentz, R., Ni, J. (1996) Grap is a novel SH3-SH2-SH3 adaptor protein that couples tyrosine kinases to the Ras pathway. J. Biol. Chem. 271, 12129-12132.
26. Brizzi, M. F., Dentelli, P., Lanfrancone, L., Rosso, A., Pelicci, P. G., Pegoraro, L. (1996) Discrete protein interactions with the Grb2/c-Cbl complex in SCF- and TPO-mediated myeloid cell proliferation. Oncogene 13, 2067-2076.
27. Wisniewski, D., Strife, A., Clarkson, B. (1996) c-kit ligand stimulates tyrosine phosphorylation of the c-Cbl protein in human hematopoietic cells. Leukemia 10, 1436-1442.
28. Sattler, M., Salgia, R., Shrikhande, G., Verma, S., Pisick, E., Prasad, K. V., Griffin, J. D. (1997) Steel factor induces tyrosine phosphorylation of CRKL and binding of CRKL to a complex containing c-kit, phosphatidylinositol 3-kinase, and p120(CBL). J. Biol. Chem. 272, 10248-10253.
29. Blume-Jensen, P., Janknecht, R., Hunter, T. (1998) The kit receptor promotes cell survival via activation of P1 3-kinase and subsequent Akt-mediated phosphorylation of Bad on Ser136. Curr. Biol. 8, 779-782.
30. Tang, B., Mano, H., Yi, T., Ihle, J. N. (1994) Tec kinase associates with c-kit and is tyrosine phosphorylated and activated following stem cell factor binding. Mol. Cell. Biol. 14, 8432-8437.
31. Jhun, B. H., Rivnay, B., Price, D., Avraham, H. (1995) The MATK tyrosine kinase interacts in a specific and SH2-dependent manner with c-Kit. J. Biol. Chem. 270, 9661-9666.
32. Alai, M., Mui, A. L., Cutler, R. L., Bustelo, X. R., Barbacid, M., Krystal, G. (1992) Steel factor stimulates the tyrosine phosphorylation of the proto-oncogene product, p95vav, in human hemopoietic cells. J. Biol. Chem. 267, 18021-18025.
33. Carpino, N., Wisniewski, D., Strife, A., Marshak, D., Kobayashi, R., Stillman, B., Clarkson, B. (1997) p62(dok): a constitutively tyrosine-phosphorylated, GAP-associated protein in chronic myelogenous leukemia progenitor cells. Cell 88, 197-204.
34. Brizzi, M., Zini, M., Aronica, M., Blechman, J., Yarden, Y., Pegoraro, L. (1994) Convergence of signaling by interleukin-3, granulocyte-macrophage colony-stimulating factor, and mast cell growth factor on JAK2 tyrosine kinase. J. Biol. Chem. 269, 31680-31684.
35. Weiler, S. R., Mou, S., DeBerry, C. S., Keller, J. R., Ruscetti, F. W., Ferris, D. K., Longo, D. L., Linnekin, D. (1996) JAK2 is associated with the c-kit proto-oncogene product and is phosphorylated in response to stem cell factor. Blood 87, 3688-3693.
36. Linnekin, D., Weiler, S. R., Mou, S., DeBerry, C. S., Keller, J. R., Ruscetti, F. W., Ferris, D. K., Longo, D. L. (1996) JAK2 is constitutively associated with c-Kit and is phosphorylated in response to stem cell factor. Acta Haematol. 95, 224-228.
37. Deberry, C., Mou, S., Linnekin, D. (1997) StatI associates with c-kit and is activated in response to stem cell factor. Biochem. J. 327 ( Pt 1), 73-80.
38. Herbst, R., Shearrnan, M. S., Jallal, B., Schiessinger, J., Ullrich, A. (1995) Formation of signal transfer complexes between stem cell and platelet-derived growth factor receptors and SH2 domain proteins in vitro. Biochemistry 34, 5971-5979.
39. Krystal, G. W., DeBerry, C. S., Linnekin, D., Litz, J. (1998) Lck associates with and is activated by Kit in a small cell lung cancer cell line: inhibition of SCF-mediated growth by the Src family kinase inhibitor PP1. Cancer Res. 58, 4660-4666.
40. Hemesath, T. J., Price, E. R., Takemoto, C., Badalian, T., Fisher, D. E. (1998) MAP kinase links the transcription factor Microphthalmia to c-Kit signalling in melanocytes. Nature 391, 298-301.
41. Takahira, H., Gotoh, A., Ritchie, A., Broxmeyer, H. E. (1997) Steel factor enhances integrin-mediated tyrosine phosphorylation of focal adhesion kinase (pp125FAK) and paxillin. Blood 89, 1574-1584.
42. Yi, T., Ihle, J. N. (1993) Association of hernatopoletic cell phosphatase with c-Kit after stimulation with c-Kit ligand. Mol. Cell. Biol. 13, 3350-3358.
43. Lorenz, U., Bergemann, A. D., Steinberg, H. N., Flanagan, J. G., Li, X., Galli, S. J., Neel, B. G. (1996) Genetic analysis reveals cell type-specific regulation of receptor tyrosine kinase c-Kit by the protein tyrosine phosphatase SHP1. J. Exp. Med. 184, 1111-1126.
44. Paulson, R., Vesely, S., Siminovitch, K., Bernstein, A. (1996) Signalling by the W/Kit receptor tyrosine kinase is negatively regulated in vivo by the protein tyrosine phosphatase Shp1. Nat. Genet. 13, 309-315.
45. Kozloxvski, M., Larose, L., Lee, F., Le, D. M., Rottapel, R., Siminovitch, K. A. (1998) SHP-1 binds and negatively modulates the c-Kit receptor by interaction with tyrosine 569 in the c-Kit juxtamembrane domain. Mol. Cell. Biol. 18, 2089-2099.
46. Blume-Jensen, P., Ronnstrand, L., Gout, I., Waterfield, M. D., Heldin, C. H. (1994) Modulation of Kit/stem cell factor receptor-induced signaling by protein kinase C. J. Biol. Chem. 269,21793-21802.
47. Blume-Jensen, P., Wemstedt, C., Heldin, C. H., Ronnstrand, L. (1995) Identification of the major phosphorylation sites for protein kinase C in kit/stem cell factor receptor in vitro and in intact cells. J. Biol. Chem. 270, 14192-14200.
48. Kozawa, O., Blume-Jensen, P., Heldin, C. H., Ronnstrand, L. (1997) Involvement of phosphatidylinositol 3'-kinase in stem-cell-factor-induced phospholipase D activation and arachidonic acid release. Eur. J. Biochem. 248, 149-155.
49. Timokhina, I., Kissel, H., Stella, G., Besmer, P. (1998) Kit signaling through P1 3-kinase and Src kinase pathways: an essential role for Raci and JNK activation in mast cell proliferation. EMBO J. 17, 6250-6262.
50. Suzuki, T., Shoji, S., Yamamoto, K., Nada, S., Okada, M., Yamamoto, T., Honda, Z. (1998) Essential roles of Lyn in fibronectin-mediated filamentous actin assembly and cell motility in mast cells. J. Immunol. 161,3694-3701.

51. Koike, T., Mizutani, T., Hirai, K., Morita, Y., Nozawa, Y. (1993) SCF/c-kit receptor-mediated arachidonic acid liberation in rat mast cells. Involvement of PLD activation associated tyrosine phosphorylation. Biochem. Biophys. Res. Commun. 197, 1570-1577.
52. Koike, T., Hirai, K., Morita, Y., Nozawa, Y. (1993) Stem cell factor-induced signal transduction in rat mast cells. Activation of phospholipase D but not phosphoinositide-specific phospholipase C in c-kit receptor stimulation. J. Immunol. 151,359-366.
53. Nagai, S., Kitani, S., Hirai, K., Takaishi, T., Nakajima, K., Kihara, H., Nonomura, Y., Ito, K., Morita, Y. (1995) Pharmacological study of stem-cell-factor-induced mast cell histamine release with kinase inhibitors. Biochem. Biophys. Res. Commun. 208, 576-581.
54. Yee, N., Hsiau, C., Serve, H., Vosseller, K., Besmer, P. (1994) Mechanism of down-regulation of c-kit receptor. Roles of receptor tyrosine kinase, phosphatidylinositol 3'-kinase, and protein kinase C. J. Biol. Chem. 269, 31991-31998.
55. Miyazawa, K., Toyama, K., Gotoh, A., Hendrie, P. C., Mantel, C., Broxmeyer, H. E. (1994) Ligand-dependent polyubiquitination of c-kit gene product: a possible mechanism of receptor down modulation in M07e cells. Blood 83, 137-145.
56. Gommerman, J. L., Rottapel, R., Berger, S. A. (1997) Phosphatidylinositol 3-kinase and Ca2+ influx dependence for ligand-stimulated internalization of the c-Kit receptor. J. Biol. Chem. 272, 30519-30525.
57. De Sepulveda, P., Okkenhaug, K., Rose, J. L., Hawley, R. G., Dubreuil, P., Rottapel, R. (1999) Socs1 binds to multiple signalling proteins and suppresses Steel factor-dependent proliferation. EMBO J. 18, 904-915.
58. Blechman, J., Lev, S., Givol, D., Yarden, Y. (1993) Structure-function analyses of the kit receptor for the steel factor. Stem Cells (Dayt) 11 Suppl 2, 12-21.
59. Tsujimura, T. (1996) Role of c-kit receptor tyrosine kinase in the development, survival and neoplastic transformation of mast cells. Pathol. Int. 46, 933-938.
60. Kitayama, H., Kanakura, Y., Furitsu, T., Tsujimura, T., Oritani, K., Ikeda, H., Sugahara, H., Mitsui, H., Kanayama, Y., Kitamura, Y., et al. (1995) Constitutively activating mutations of c-kit receptor tyrosine kinase confer factor-independent growth and tumorigenicity of factor-dependent hematopoietic cell lines. Blood 85, 790-798.
61. Tsujimura, T., Hashimoto, K., Kitayama, H., Ikeda, H., Sugahara, H., Matsumura, I., Kaisho, T., Terada, N., Kitamura, Y., Kanakura, Y. (1999) Activating mutation in the catalytic domain of c-kit elicits hematopoietic transformation by receptor self-association not at the ligand-induced dimerization site. Blood 93, 1319-1329.
62. Piao, X., Paulson, R., van der Geer, P., Pawson, T., Bernstein, A. (1996) Oncogenic mutation in the Kit receptor tyrosine kinase alters substrate specificity and induces degradation of the protein tyrosine phosphatase SHP-1. Proc. Nati. Acad. Sci. USA 93, 14665-14669.
63. Songyang, Z., Shoelson, S. E., McGlade, J., Olivier, P., Pawson, T., Bustelo, X. R., Barbacid, M., Sabe, H., Hanafusa, H., Yi, T., et al. (1994) Specific motifs recognized by the SH2 domains of Csk, 3BP2, fps/fes, GRB-2, HCP, SHC, Syk, and Vav. Mol. Cell. Biol. 14, 2777-2785.
64. Songyang, Z., Gish, G., Mbamalu, G., Pawson, T., Cantley, L. C. (1995) A single point mutation switches the specificity of group III Src homology (SH) 2 domains to that of group I SH2 domains. J. Biol. Chem. 270, 26029-26032.
65. Hofstra, R. M., Landsvater, R. M., Ceccherini, I., Stulp, R. P., Stelwagen, T., Luo, Y., Pasini, B., Hoppener, J. W., van Amstel, H. K., Romeo, G., et al. (1994) A mutation in the RET proto-oncogene associated with multiple endocrine neoplasia type 2B and sporadic medullary thyroid carcinoma. Nature 367, 375-376.
66. Hanks, S. K., Quinn, A. M., Hunter, T. (1988) The protein kinase family: conserved features and deduced phylogeny of the catalytic domains. Science 241, 42-52.
67. Knighton, D. R., Zheng, J. H., Ten Eyck, L. F., Xuong, N. H., Taylor, S. S., Sowadski, J. M. (1991) Structure of a peptide inhibitor bound to the catalytic subunit of cyclic adenosine monophosphate-dependent protein kinase. Science 253, 414-420.

The invention claimed is:

1. A screening method for identifying compounds that are selective inhibitors of c-kit, which comprises:
   a) bringing into contact (i) stem cell factor (SCF)-activated c-kit or constitutively activated c-kit and (ii) at least one compound to be tested,
   b) determining whether the at least one compound inhibits said SCF-activated c-kit or constitutively activated c-kit,
   c) selecting compounds that inhibit said SCF-activated c-kit or constitutively activated c-kit,
   d) testing a subset of compounds selected in step c) for ability to promote death of IL-3 dependent cells cultured in the presence of IL-3, and
   e) selecting a subset of compounds tested in step d), which are unable to promote death of said IL-3 dependant cells cultured in presence of IL-3.

2. A screening method according to claim 1, wherein said SCF-activated c-kit or constitutively activated c-kit is said constitutively activated c-kit.

3. A screening method according to claim 2, further comprising the steps of testing a subset of compounds selected in step c) that are inhibitors of constitutively activated c-kit for ability to inhibit SCF-activated c-kit, and selecting a subset of compounds selected in step c), which are capable of inhibiting said SCF-activated c-kit.

4. A screening method according to claim 1, wherein said SCF-activated c-kit or constitutively activated c-kit is said SCF-activated c-kit.

5. A screening method according to claim 1, wherein compounds in step a) are tested at a concentration above 10 μM.

6. A screening method according to claim 1, wherein IL-3 is present in culture media of IL-3 dependant cells at a concentration between 0.5 and 10 ng/ml.

7. A screening method according to claim 6, wherein IL-3 is present in the culture media of IL-3 dependant cells at a concentration of between 1 to 5 ng/ml.

8. A screening method according to one of claims 6 and 7, wherein the IL-3 dependant cells are mast cells or transfected mast cells.

9. A screening method according to claim 1, wherein the constitutively activated c-kit in step a) is D816V, D816Y, D816F or D820G mutant c-kit.

10. A screening method according to claim 1, wherein the extent to which component (ii) inhibits activated c-kit is measured by determining c-kit phosphorylation in vitro or by determining ex vivo cell proliferation.

11. A screening method according to claim 1, wherein said at least one compound to be tested in step a) of claim 1 is tested for inhibition of SCF-activated c-kit at a concentration of less than 1 μM.

12. A screening method according to claim 11, wherein the extent to which said compounds inhibit SCF-activated c-kit is measured by determining c-kit phosphorylation in vitro or by determining ex vivo cell proliferation.

13. A screening method according to claim 1, wherein the inhibition of constitutively activated c-kit or SCF-activated c-kit is determined by assaying for c-kit phosphorylation.

14. A screening method for identifying compounds that are selective inhibitors of c-kit comprising:
  a) contacting cells expressing a constitutively activated c-kit with a plurality of test compounds,
  b) identifying a subset of candidate compounds targeting said constitutively activated c-kit, each having an IC50<10 μM, by measuring the extent of cell death,
  c) contacting IL-3 dependent cells cultured in the presence of IL-3 expressing c-kit with said subset of candidate compounds identified in step b),
  d) identifying a subset of candidate compounds targeting specifically c-kit by identifying compounds which are unable to promote death of said IL-3 dependent cells cultured in presence of IL-3, and
  e) contacting cells expressing SCF-activated c-kit with said subset of compounds unable to promote death of said IL-3 dependent cells of step d), and further selecting a subset of candidate compounds targeting SCF-activated c-kit, wherein each candidate compound has an IC50<10 μM by measuring the extent of cell death.

15. A screening method according to claim 14, wherein the extent of cell death is measured by 3H thymidine incorporation, trypan blue exclusion or flow cytometry with propidium iodide.

16. The method of claim 14, wherein the IC50 in step e) is less than 1 μM.

17. A screening method according to claim 1 or 14, wherein said compounds are tyrosine kinase inhibitors.

18. A screening method according claim 1 or 14, wherein said compounds are selected from the group consisting of indolinone, pyrimidine derivatives, pyrrolopyrimidine derivatives, quinazoline derivatives, quinoxaline derivatives, pyrazole derivatives, bis monocyclic, bicyclic or heterocyclic aryl compounds, vinylene-azaindole derivatives and pyridyl-quinolone derivatives, styryl compounds, styryl-substituted pyridyl compounds, seleoindoles, selenides, tricyclic polyhydroxylic compounds and benzylphosphonic acid compounds.

19. A screening method according to claim 1 or 14, wherein said compounds are pyrimidine derivatives.

20. The screening method according to claim 19, wherein said pyrimidine derivatives are N-phenyl-2-pyrimidine-amine derivatives.

21. A screening method according to claim 1 or 14, wherein said compounds are indolinone derivatives.

22. The screening method according to claim 21, wherein said indolinone derivatives are pyrrol-substituted indolinones.

23. A screening method according to claim 1 or 14, wherein said compounds are monocyclic, bicyclic aryl and heteroaryl compounds.

24. A screening method according to claim 1 or 14, wherein said compounds are quinazoline derivatives.

* * * * *